(12) United States Patent
Lechner et al.

(10) Patent No.: US 6,579,972 B1
(45) Date of Patent: Jun. 17, 2003

(54) EXTRACELLULAR SIGNAL-REGULATED KINASE, SEQUENCES, AND METHODS OF PRODUCTION AND USE

(75) Inventors: Cornelia Lechner, Unterschleissheim (DE); Niels Peter Møller, Copenhagen (DK); Axel Ullrich, Martinsried (DE)

(73) Assignee: Max-Planck-Gesellschaft zur Forderung der Wissenschaften, e.V., Munich (DE)

(*) Notice: Subject to any disclaimer, the term of this patent is extended or adjusted under 35 U.S.C. 154(b) by 0 days.

(21) Appl. No.: 09/393,212

(22) Filed: Sep. 9, 1999

Related U.S. Application Data

(60) Division of application No. 08/459,953, filed on Jun. 2, 1995, now Pat. No. 6,030,822, which is a continuation-in-part of application No. 08/029,404, filed on Mar. 19, 1993, now Pat. No. 5,459,036.

(51) Int. Cl.$^7$ .......................... C07K 16/40; C12N 5/12

(52) U.S. Cl. ..................... 530/388.26; 530/389.1; 530/809; 530/388.1; 435/7.92

(58) Field of Search .................. 530/387.1, 388.1, 530/809, 388.26, 389.1; 435/7.1, 7.92

(56) References Cited

U.S. PATENT DOCUMENTS

| | | |
|---|---|---|
| 5,219,748 A | 6/1993 | Yoshitaka et al. |
| 5,512,473 A | 4/1996 | Brent et al. |

FOREIGN PATENT DOCUMENTS

| | | |
|---|---|---|
| WO | 91/19008 | 12/1991 |
| WO | 92/13001 | 8/1992 |
| WO | 92/21641 | 12/1992 |
| WO | 92/21660 | 12/1992 |
| WO | 93/23569 | 11/1993 |

OTHER PUBLICATIONS

Sambrook et al. Molecular Cloning: A Laboratory Manual Second Edition vols. 1, 2 and 3. Cold Spring Harbor Laboratory Press: Cold Spring Harbor, New York, U.S.A. Nov., 1989, p. 18.70.*

Ahn et al., "Evidence for an Epidermal Growth Factor–stimulated Protein Kinase Cascade in Swiss 3T3 Cells," *The Journal of Biological Chemistry* 265(20):11495–11501 (1990).

Ahn et al., "Identification of Multiple Epidermal Growth Factor–stimulated Protein Serine/Threonine Kinases from Swiss 3T3 Cells," *Journal of Biological Chemistry* 265(20):11487–11494 (1990).

Ballou et al., "Protein Phosphatase 2A Inactivates the Mitogen–stimulated S6 Kinase from Swiss Mouse 3T3 Cells," *The Journal of Biological Chemistry* 263(3):1188–1194 (1988).

Borthwick et al., "Protein–serine kinase from rat epididymal adipose tissue which phosphorylates and activates acetyl–CoA carboxylase," *Biochem. J.* 270:795–801 (1990).

Boulton et al., "An Insulin–Stimulated Protein Kinase Similar to Yeast Kinases Involved in Cell Cycle Control," *Science* 249:64–67 (1990).

Boulton et al., "ERKs: A Family of Protein–Serine/Threonine Kinases That Are Activated and Tyrosine Phosphorylated in Response to Insulin and NGF," *Cell* 65:663–675 (1991).

Boulton et al., "Purification and Properties of Extracellular Signal–Regulated Kinase 1, an Insulin–Stimulated Microtubule–Associated Protein 2 Kinase," *Biochemistry* 30:278–286 (1991).

Boulton et al., *Cell Regulation* 2:357–371 (1991).

Charles et al., "The growth factor–inducible immediate–early gene 3CH134 encodes a protein–tyrosine–phosphatase," *Proc. Natl. Acad. Sci. USA* 90:5292–5296 (1993).

Chung et al., "Mitogen–activated Swiss mouse 3T3 RSK kinases I and II are related to pp44$^{mpk}$ from sea star oocytes and participate in the regulation of pp90$^{rsk}$ activity," *Proc. Natl. Acad. Sci. USA* 88:4981–4985 (1991).

Cicirelli et al., "Activation of Multiple Protein Kinases during the Burst in Protein Phosphorylation That Precedes the First Meiotic Cell Division in Xenopus Oocytes*," *The Journal of Biological Chemistry* 263(4):2009–2019 (1988).

Cobb et al., *Cell Regulation* 2:965–978 (1991).

Cooper et al., "Diverse Mitogenic Agents Induce the Phosphorylation of Two Related 42,000–Dalton Proteins on Tyrosine in Quiescent Chick Cells," *Molecular and Cellular Biology* 4(1):30–37 (1984).

(List continued on next page.)

Primary Examiner—David S. Romeo
(74) Attorney, Agent, or Firm—Beth A. Burrous; Foley & Lardner

(57) ABSTRACT

The present invention relates, in general, to an extracellular signal regulated kinase, ERK-5. In particular, the present invention relates to nucleic acid molecules coding for ERK-5; ERK-5 polypeptides; recombinant nucleic acid molecules; cells containing the recombinant nucleic acid molecules; antisense ERK-5 nucleic acid constructs; antibodies having binding affinity to an ERK-5 polypeptide; hybridomes containing the antibodies; nucleic acid probes for the detecting of ERK-5 nucleic acid; a method of detecting ERK-5 nucleic acid or polypeptide in a sample; kits containing nucleic acid probes or antibodies; a method of detecting a compound capable of binding to ERK-5 or a fragment thereof; a method of detecting an agonist or antagonist of ERK-5 activity; a method of agonizing or antagonizing ERK-5 associated activity in a mammal; a method of treating diabetes mellitus, skeletal muscle diseases, Alzheimer's disease, or peripheral neuropathies in a mammal with an agonist or antagonist of ERK-5 activity; and a pharmaceutical composition comprising an ERK-5 agonist or antagonist.

10 Claims, 5 Drawing Sheets

OTHER PUBLICATIONS

Dent et al., "The molecular mechanism by which insulin stimulates glycogen synthesis in mammalian skeletal muscle," *Nature* 348:302–308 (1990).

Duerr et al., "MsERK1: A Mitogen–Activated Protein Kinase from a Flowering Plant," *The Plant Cell* 5:87–96 (1993).

Ershler et al., *Gene* 124:305–306 (1993).

Ferrell and Martin, "Identification of a 42–Kilodalton Phosphotyrosyl Protein as a Serine(Threonine) Protein Kinase by Renaturation," *Molecular and Cellular Biology* 10(6):3020–3026 (1990).

Gotoh et al., "In vitro effects of microtubule dynamics of purified Xenopus M phase–activated MAP kinase," *Nature* 349:251–254 (1991).

Gotoh et al., "Xenopus M phase MAP kinase: isolation of its cDNA and activation by MPF," *The EMBO Journal* 10(9):2661–2668 (1991).

Gregory et al., "An Insulin–stimulated Ribosomal Protein S6 Kinase from Rabbit Liver," *The Journal of Biological Chemistry* 264(31):18397–18401 (1989).

Hanks et al., "The Protein Kinase Family: Conserved Features and Deduced Phylogeny of the Catalytic Domains," *Science* 241:42–52 (1988).

Her et al., "Sequence of pp42/MAP kinase, a serine/threonine kinase regulated by tyrosine phosphorylation," *Nucleic Acids Research* 19(13):3743 (1991).

Hoshi et al., "Activation of $Ca^{2+}$–inhibitable Protein Kinase That Phosphorylates Microtuble–associated Protein 2 in Vitro by Growth Factors, Phorbol Esters, and Serum in Quiescent Cultured Human Fibroblasts," *Journal of Biological Chemistry* 263:5396–5401 (1988).

Kozak et al., "An analysis of 5'–noncoding sequences from 699 vertebrate messenger RNAs," *Nucleic Acids Research* 15:8125–8148 (1987).

Kyriakis and Avruch, "pp54 Microtubule–associated Protein 2 Kinase: A Novel Serine/Threonine Protein Kinase Regulated by Phosphorylation and Stimulated by Poly–L–Lysine," *Journal Biological Chemistry* 265:17355–17363 (1990).

Kyriakis et al., "pp54 Microtubule–associated Protein–2 Kinase Requires Both Tyrosine an Serine/Threonine Phosphorylation for Activity," *Journal Biological Chemistry* 226:10043–10046 (1991).

Needleman and Wunsch, "A General Method Applicable to the Search for Similarities in the Amino Acid Sequence of Two Proteins," *J. Mol. Biol.* 48:443–453 (1970).

Northwood et al., "Isolation and Characterization of Two Growth Factor–stimulated Protein Kinases That Phosphorylate the Epidermal Growth Factor Receptor at Threonine 669," *Journal of Biological Chemistry* 266:15266–15276 (1991).

Owaki et al., "Extracellular Signal–Regulated Kinases in T Cell Characterization of Human ERK1 and ER2 cDNAs[1,2]," *Biochemical and Biophysical Research Communications* 183:1416–1422 (1992).

Payne et al., "Identification of the regulatory phosphorylation sites in pp42/mitogen–activated protein kinase (MAP kinase)," *EMBO J.* 10:885–892 (1991).

Posada and Cooper, "Requirements for Phosphorylation of MAP Kinase During Meiosis in Xenopus Oocytes," *Science* 255:212–215 (1992).

Posada et al., "Tyrosine Phosphorylation and Activation of Homologous Protein Kinases during Oocyte Maturation and Mitogenic Activation of Fibroblasts," *Molecular and Cellular Biology* 11:2517–2528 (1991).

Ray and Sturgill, "Characterization of Insulin–stimulated Microtubule–associated Protein Kinase," *The Journal of Biological Chemistry* 263:12721–12727 (1988).

Ray and Sturgill, "Insulin–stimulated microtubule–associated protein kinase is phosphorylated on tyrosine and threonine in vivo," *Proc. Natl. Acad. Sci. USA* 85:3753–3757 (1988).

Ray and Sturgill, "Rapid stimulation by insulin of a serine/threonine kinase in 3T3–L1 adipocytes that phosphorylates microtubule–associated protein 2 in vitro," *Proc. Natl. Acad. Sci. USA* 84:1502–1506 (1987).

Rossomando et al., "Evidence that pp42, a major tyrosine kinase target protein, is a mitogen–activated serine/threonine protein kinase," *Proc. Natl. Acad. Sci. USA* 86:6940–6943 (1989).

Sanghera et al., "Identification of the sites in myelin basic protein that are phosphorylated by meiosis–activated protein kinase $p44^{mpk}$," *FEBS Letters* 273:223–226 (1990).

Seger et al., "Microtubule–associated protein 2 kinases, ERK1 and ERK2, undergo autophosphorylation on both tyrosine and threonine residues: Implications for their mechanism of activation," *Proc. Natl. Acad. Sci. USA* 88:6142–6146 (1991).

Steer et al., "Regulation of pathways of glucose metabolism in kidney: Specific linking of pentose phosphate pathway activity with kidney growth in experimental diabetes and unilateral nephrectomy," *FEBS Letters* 150:494–498 (1982).

Sturgill and Wu, "Recent progress in characterization of protein kinase cascades for phosphorylation of ribosomal protein S6," *Biochimica et Biophysica Acta* 1092:350–357 (1991).

Sturgill et al., "Insulin–stimulated MAP–2 kinase phosphorylates and activates ribosomal protein S6 kinase II," *Nature* 334:715–718 (1988).

Sun et al., "MKP–1 (3CH134), am Immediate Early Gene Product, Is a Dual Specifity Phosphatase That Dephosphorylates MAP Kinase In Vivo," *Cell* 75:487–493 (1993).

Tsao and Green, "The Roles of Macromolecular Synthesis and Phosphorylation in the Regulation of a Protein Kinase Activity Transiently Stimulated by Nerve Growth Factor," *The Journal of Biological Chemistry* 266:12981–12988 (1991).

* cited by examiner

```
  1   ggctctgcggggtgggcagctcccgggcctgccatgagctctccgccgcccggxggcagt
      ---------+---------+---------+---------+---------+---------+ 60
      ccgagacgccccacccgtcgagggcccggacggtactcgagaggcggcgggccxccgtca
                                      M   S   S   P   P   P   G   G   S   -

61   ggcttttaccgccaggaggtgaccaagacggcctgggaggtgcgcgccgtgtaccgggac
      ---------+---------+---------+---------+---------+---------+ 120
      ccgaaaatggcggtcctccactggttctgccggaccctccacgcgcggcacatggccctg
  a    G   F   Y   R   Q   E   V   T   K   T   A   W   E   V   R   A   V   Y   R   D   -

121   ctgcagcccgtgggctcgggcgcctacggcgcggtgtgctcggccgtggacggccgcacc
      ---------+---------+---------+---------+---------+---------+ 180
      gacgtcgggcacccgagcccgcggatgccgcgccacacgagccggcacctgccggcgtgg
  a    L   Q   P   V   G   S   G   A   Y   G   A   V   C   S   A   V   D   G   R   T   -

181   ggcgctaaggttgccatcaagaagctgtatcggcccttccagtccgagctgttcgccaag
      ---------+---------+---------+---------+---------+---------+ 240
      ccgcgattccaacggtagttcttcgacatagccgggaaggtcaggctcgacaagcggttc
  a    G   A   K   V   A   I   K   K   L   Y   R   P   F   Q   S   E   L   F   A   K   -

241   ctcgcctaccgcgagctgcgcctgctcaagcacatgcgccacgagaacgtgatcgggctg
      ---------+---------+---------+---------+---------+---------+ 300
      gagcggatggcgctcgacgcggacgagttcgtgtacgcggtgctcttgcactagcccgac
  a    L   A   Y   R   E   L   R   L   L   K   H   M   R   H   E   N   V   I   G   L   -

301   ctggacgtattcactcctgatgagaccctggatgacttcacggacttttacctggtgatg
      ---------+---------+---------+---------+---------+---------+ 360
      gacctgcataagtgaggactactctgggacctactgaagtgcctgaaaatggaccactac
  a    L   D   V   F   T   P   D   E   T   L   D   D   F   T   D   F   Y   L   V   M   -

361   ccgttcatgggcaccgacctgggcaagctcatgaaacatgagaagctaggcgaggaccgg
      ---------+---------+---------+---------+---------+---------+ 420
      ggcaagtacccgtggctggacccgttcgagtactttgtactcttcgatccgctcctggcc
  a    P   F   M   G   T   D   L   G   K   L   M   K   H   E   K   L   G   E   D   R   -

421   atccagttcctcgtgtaccagatgatgaagggggctgaggtatatccacgctgccggcatc
      ---------+---------+---------+---------+---------+---------+ 480
      taggtcaaggagcacatggtctactacttccccgactccatataggtgcgacggccgtag
  a    I   Q   F   L   V   Y   Q   M   M   K   G   L   R   Y   I   H   A   A   G   I   -

481   atccacagagacctgaagcccggcaacctggctgtgaacgaagactgtgagctgaagatc
      ---------+---------+---------+---------+---------+---------+ 540
      taggtgtctctggacttcgggccgttggaccgacacttgcttctgacactcgacttctag
  a    I   H   R   D   L   K   P   G   N   L   A   V   N   E   D   C   E   L   K   I   -
```

FIG. 1a

```
541  ctggacttcggcctggccaggcaggcagacagtgagatgactgggtacgtggtgacccgg
     ---------+---------+---------+---------+---------+---------+ 600
     gacctgaagccggaccggtccgtccgtctgtcactctactgacccatgcaccactgggcc a     L  D  F  G  L  A  R  Q  A  D  S  E  M  T  G  Y  V  V  T  R   -

601  tggtaccgggctcccgaggtcatcttgaattggatcgcgtacacgcagacggtggacatc
     ---------+---------+---------+---------+---------+---------+ 660
     accatggcccgagggctccagtagaacttaacctagcgcatgtgcgtctgccacctgtag a     W  Y  R  A  P  E  V  I  L  N  W  I  A  Y  T  Q  T  V  D  I   -

661  tggtctgtgggctgcatcatggcggagatgatcacaggcaagacgctgttcaagggcagc
     ---------+---------+---------+---------+---------+---------+ 720
     accagacacccgacgtagtaccgcctctactagtgtccgttctgcgacaagttcccgtcg a     W  S  V  G  C  I  M  A  E  M  I  T  G  K  T  L  F  K  G  S   -

721  gaccacctggaccagctgaaggagatcatgaaggtgacggggacgcctccggctgagttt
     ---------+---------+---------+---------+---------+---------+ 780
     ctggtggacctggtcgacttcctctagtacttccactgccnctgcggaggccgactcaaa a     D  H  L  D  Q  L  K  E  I  M  K  V  T  G  T  P  P  A  E  F   -

781  gtgcagcggctgcagagcgatgaggccaagaactacatgaagggcctccccgaattggag
     ---------+---------+---------+---------+---------+---------+ 840
     cacgtcgccgacgtctcgctactccggttcttgatgtacttcccggaggggcttaacctc a     V  Q  R  L  Q  S  D  E  A  K  N  Y  M  K  G  L  P  E  L  E   -

841  aagaaggattttgcctctatcctgaccaatgcaagccctctggctgtgaacctcctggag
     ---------+---------+---------+---------+---------+---------+ 900
     ttcttcctaaaacggagataggactggttacgttcgggagaccgacacttggaggacctc a     K  K  D  F  A  S  I  L  T  N  A  S  P  L  A  V  N  L  L  E   -

901  aagatgctggtgctggacgcggacatcaggttgactgcaggcgagtttctttttcccatccc
     ---------+---------+---------+---------+---------+---------+ 960
     ttctacgaccacgacctgcgcctgtagtccaactgacgtccgctcaaagaaagggtaggg a     K  M  L  V  L  D  A  D  I  R  L  T  A  G  E  F  L  S  H  P   -

961  tacttcgagtccctgcacgacacggaagatgagccccaggtccagaagtatgatgactcc
     ---------+---------+---------+---------+---------+---------+ 1020
     atgaagctcagggacgtgctgtgccttctactcggggtccaggtcttcatactactgagg a     Y  F  E  S  L  H  D  T  E  D  E  P  Q  V  Q  K  Y  D  D  S   -

1021 tttgactactttgaccgcacactggatgaatggaagccgtgttacttacaaagaggtgct
     ---------+---------+---------+---------+---------+---------+ 1080
     aaactgatgaaactggcgtgtgacctacttaccttcggcacaatgaatgtttctccacga a     F  D  Y  F  D  R  T  L  D  E  W  K  P  C  Y  L  Q  R  G  A   -
```

FIG. 1b

```
      cagcttcaagcctccccggcagctgggggccagggtctccaaggagacgcctctgtgaag
1081  ------+---------+---------+---------+---------+---------+ 1140
      gtcgaagttcggagggggccgtcgaccccggtcccagaggttcctctgcggagacacttc a      Q  L  Q  A  S  P  A  A  G  G  Q  G  L  Q  G  D  A  S  V  K   - atctctgggctccggggtggcagtgaggaccaccttcaccttccacctgagaggggactc
1141  ------+---------+---------+---------+---------+---------+ 1200
      tagagacccgaggccccaccgtcactcctggtggaagtggaaggtggactctcccctgag a      I  S  G  L  R  G  G  S  E  D  H  L  H  L  P  P  E  R  G  L   - tcgttgccaccttgaccttggctggggcttgcatcccaaggcatccatcagagcagacgc
1201  ------+---------+---------+---------+---------+---------+ 1260
      agcaacggtggaactggaaccgaccccgaacgtagggttccgtaggtagtctcgtctgcg a      S  L  P  P  *                                                -
```

FIG. 1c

|        |            |            |            |            | 50         |
|--------|------------|------------|------------|------------|------------|
| HERK5  | .......... | .GSAGWAAPG | PAMSSPPPTR | SGFYRQEVTK | TAWEVRAVYR |
| HERK1  | .......... | .......... | ......PGE  | VEMVKGQP.. | ..FDVGPRYT |
| HERK2  | GAAAERRAQR | GGGGGGPAAN | MAAAAAAGAG | PEMVRGQV.. | ..FDVGPRYT |
| HERK3  | GARGRPLAET | WPFLTAPVLP | GQLQITEPTM | AEKGDCIASV | YGYDLGGRFV |

|        | I          |            | II         | III        | 100        |
|--------|------------|------------|------------|------------|------------|
| HERK5  | DLQPVGSGAY | GAVCSAVDGR | TGAKVAIKKL | YRPFQSELFA | KLAYRELRLL |
| HERK1  | QLQYIGEGAY | GMVSSAYDHV | RKTRVAIKKI | .SPFEHQTYC | QRTLREIQIL |
| HERK2  | NLSYIGEGAY | GMVCSAYDNV | NKVRVAIKKI | .SPFEHQTYC | QRTLREIKIL |
| HERK3  | DFQPLGFGVN | GLVLSAVDSR | ACRKVAVKKI | ..ALSDARSM | KHALREIKII |

|        |            | IV         |            | V          | 150        |
|--------|------------|------------|------------|------------|------------|
| HERK5  | KHMRHENVIG | LLDVFTPDET | .....LDDFT | DFYLVMPFMG | TDLGKLMKHE |
| HERK1  | LRFRHENVIG | IRDIL.RAST | ......LEAMR | DVYIVQDLME | TDLYKLLKSQ |
| HERK2  | LRFRHENIIG | INDII.QAPT | ......IEQMK | DVYIVQDLME | TDLYKLLKTQ |
| HERK3  | RRLDHDNIVK | VYEVLGPKGT | DLQGELFKFS | VAYIVQEYME | TDLARLLEQG |

|        | VIA        |            | VIB        |            | 200        |
|--------|------------|------------|------------|------------|------------|
| HERK5  | KLGEDRIQFL | VYQMMKGLRY | IHAAGIIHRD | LKPGNLAVNE | DC.ELKILDF |
| HERK1  | QLSNDHICYF | LYQILRGLKY | IHSANVLHRD | LKPSNLLINT | TC.DLKICDF |
| HERK2  | HLSNDHICYF | LYQILRGLKY | IHSANVLHRD | LKPSNLLLNT | TC.DLKICDF |
| HERK3  | TLAEEHAKLF | MYQLLRGLKY | IHSANVLHRD | LKPANIFIST | EDLVLKIGDF |

|        | VII        | *          | VIII       | IX         | 250        |
|--------|------------|------------|------------|------------|------------|
| HERK5  | GLARQADSE. | .....MTGYV | VTRWYRAPEV | ILNWIAYTQT | VDIWSVGCIM |
| HERK1  | GLARIADPEH | DHTGFLTEYV | ATRWYRAPEI | MLNSKGYTKS | IDIWSVGCIL |
| HERK2  | GLARVADPDH | DHTGFLTEYV | ATRWYRAPEI | MLNSKGYTKS | IDIWSVGCIL |
| HERK3  | GLARIVDQHY | SHKGYLSEGL | VTKWYRSPRL | LLSPNNYTKA | IDMWAAGCIL |

FIG. 2a

```
                                                            X                                              300
HERK5    AEMITGKTLF  KGSDHLDQLK  EIMKVTGTPP  AEFVQRLQSD  EAKNYMKGLP
HERK1    AEMLSNRPIF  PGKHYLDQLN  HILGILGSPS  QEDLNCIINM  KARNYLQSLP
HERK2    AEMLSNRPIF  PGKHYLDQLN  HILGILGSPS  QEDLNCIINL  KARNYLLSLP
HERK3    AEMLTGRMLF  AGAHELEQMQ  LILETIPVIR  EEDKDELLRV  MPS..FVSST

XI                                                                     350
HERK5    ELEKKDFASI  LTNASPLAVN  LLEKMLVLDA  DIRLTAGEFL  SHPYFESLHD
HERK1    SKTKVAWAKL  FPKSDSKALD  LLDRMLTFNP  NKRITVEEAL  AHPYLEQYYD
HERK2    HKNKVPWNRL  FPNADSKALD  LLDKMLTFNP  HKRIEVEQAL  AHPYLEQYYD
HERK3    WEVKRPLRKL  LPEVNSEAID  FLEKILTFNP  MDRLTAEMGL  QHPYMSPYSC

400
HERK5    TEDEPQVQ..  .KYDDSFDYF  DRTLDEWKPC  YLQRG..AQL  QAS.......
HERK1    PTDEPVAEEP  FTFAMELDDL  PK..ERLKEL  IFQET..ARF  QPGVLEAP*.
HERK2    PSDEPIAEAP  FKFDMELDDL  PK..EKLKEL  IFEET..ARF  QPGYRS*.
HERK3    PEDEPTSQHP  FRIEDEIDDI  VLMAANQSQL  SNWDTCSSRY  PVSLSSDLEW

450
HERK5    .....PAAGG  QGLQGDASVK  IS.GLRGGSE  DHLHLPPERG  LSLPP*
HERK3    RPDRCQDASE  VQRDPRGFGA  LAEDVQVDPR  KDSHSSSERF  LEQSHSSMER

500
HERK3    AFEADYGRSC  DYKVGSPSYL  DKLLWRDNKP  HHYSEPKLIL  DLSHWKQAAG

550
HERK3    APPTATGLAD  TGAREDEPAS  LFLEIAQWVK  STQGAQSTPA  RPPTTPSAAC

600
HERK3    LPRPPPPGPG  GRRRQPPVRP  GRVHLPRPEA  LHQARGPAGQ*

FIG. 2b
```

EXTRACELLULAR SIGNAL-REGULATED KINASE, SEQUENCES, AND METHODS OF PRODUCTION AND USE

RELATED APPLICATIONS

This application is a divisional of U.S. patent application Ser. No. 08/459,953, filed Jun. 2, 1995, now U.S. Pat. No. 6,030,822 by Lechner et al., and entitled "EXTRACELLULAR SIGNAL-REGULATED KINASE, SEQUENCES, AND METHODS OF PRODUCTION AND USE", which in turn is a continuation-in-part of U.S. application Ser. No. 08/029,404, filed Mar. 19, 1993, by Lechner et al., and entitled "EXTRACELLULAR SIGNAL-REGULATED KINASE, SEQUENCES, AND METHODS OF PRODUCTION AND USE," now U.S. Pat. No. 5,459,036, issued Oct. 17, 1995, both of which are hereby incorporated by reference herein in their entirety, including any drawings.

FIELD OF THE INVENTION

The present invention relates to the field of extracellular signal regulated kinases (ERKs), which are also referred to as mitogen-activated protein (MAP) kinases.

BACKGROUND OF THE INVENTION

None of the following discussion of the background of the invention is admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine phosphatases (TPs) and tyrosine kinases (TKs), including receptor tyrosine kinases and non-receptor tyrosine kinases.

Receptor tyrosine kinases (RTKs) belong to a family of transmembrane proteins and have been implicated in cellular signaling pathways. The predominant biological activity of some RTKs is the stimulation of cell growth and proliferation, while other RTKs are involved in arresting growth and promoting differentiation. In some instances, a single tyrosine kinase can inhibit, or stimulate, cell proliferation depending on the cellular environment in which it is expressed.

RTKs are composed of at least three domains: an extracellular ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. Individual phosphotyrosine residues of the cytoplasmic domains of receptors may serve as specific binding sites that interact with a host of cytoplasmic signaling molecules, thereby activating various signal transduction pathways.

The intracellular, cytoplasmic, non-receptor protein tyrosine kinases do not contain a hydrophobic transmembrane domain or an extracellular domain and share non-catalytic. domains in addition to sharing their catalytic kinase domains. Such non-catalytic domains include the SH2 domains and SH3 domains. The non-catalytic domains are thought to be important in the regulation of protein-protein interacions during signal transduction.

A central feature of signal transduction is the reversible phosphorylation of certain proteins. Receptor phosphorylation stimulates a physical association of the activated receptor with target molecules, which either are or are not phosphorylated. Some of the target molecules such as phospholipase Cγ are in turn phosphorylated and activated. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras. The secondary signal transducer molecules generated by activated receptors result in a signal cascade that regulates cell functions such as cell division or differentiation. Reviews describing intracellular signal transduction include Aaronson, *Science*, 254:1146–1153, 1991; Schlessinger, *Trends Biochem. Sci.*, 13:443–447, 1988; and Ullrich and Schlessinger, *Cell*, 61:203–212, 1990.

A variety of mitogens as well as tumor promoters and agents which cause cellular differentiation can initiate a signalling cascade leading to phosphorylation and activation of mitogen-activated protein (MAP) kinases (also called ERKs). Boulton et al., *Biochemistry* 30:278–286(1991) and Boulton et al., *Science* 249:64–65 (1990) describe the purification and cloning of a MAP2/MBP kinase which they named extracellular signal-regulated kinase 1 (ERK-1). Using probes derived from ERK-1, two novel kinases were identified, ERK-2 and ERK-3 (Boulton and Cobb, *Cell Regulation* 2:357–371, 1991; Boulton et al., *Cell* 65:663–675, 1991). A fourth ERK has been briefly described (Cobb et al., *Cell* Regulation 2:965–978, 1991 and WO 91/19008 published Dec. 12, 1991). These proline-site-directed serine-threonine kinases in turn phosphorylate transcription factors such as p65TCF/Elk-1, c-jun and c-myc and thus appear to play a crucial role in signal transduction by converting extracellular stimuli into transcriptional activation.

The mechanism of activation of MAP kinases has been intensively investigated and revealed a conserved signalling cascade initiated by ligand induced activation of receptor tyrosine kinases which leads to a sequential activation of a series of protein kinases. The activated growth factor receptor signals via ras to the serine-threonine kinase raf which directly activates the MAP-kinase-ERK-kinase MEK. MAP kinases are stimulated by phophorylation on two regulatory threonine and tyrosine residues, respectively, which is catalyzed by activated MEK. Upon activation, MAP kinases have been reported to translocate into the nucleus and phosphorylate transcription factors. Another substrate of MAP kinases is the S6 kinase II (pp90 rsk) which is activated by ERKs and might then control protein translation. MAP kinases can also be activated by TPA which stimulates PKC and signals to MEK via raf. However, this pathway appears to be dependent on ras. A negative regulator of MAP kinase activity has been identified by cloning of a dual specificity phosphatase encoded by an immediate early gene (Charles et al. 1993, PNAS 90, 5292–5296) that seems to be highly specific for MAP kinases (Sun et al. 1993, Cell 75, 487–493).

One or more signal transduction pathways are belleived to control the differentiation of myoblasts. Upon depletion of serum growth factors from the culture medium at high cell density, proliferating skeletal myoblasts cease DNA synthesis, start to express muscle-specific genes (biochemical differentiation) and fuse to form multinucleate myotubes (terminal differentiation). However, upon terminal differentiation, myoblasts loose their ability to reenter the cell cycle in response to growth factor stimulation. This presumably involves the retinoblastoma gene product pRB and its interaction with members of the basic helix-loop-helix myogenic factor family.

While some of these muscle specific transcription factors, namely MyoD and myf5, are constitutively expressed both in cycling myoblasts as well as in myotubes, myogenin expression is induced when myoblasts start to differentiate. However, not only transcriptional regulation, but also post-translational modification such as phosphorylation which has been reported for MyoD1 and myogenin as well as myf5 may influence commitment to myogenesis and maintenance of the differentiated state. Activated oncogenes like ras and src as well as growth factors which are involved in or initiate signal transduction, inhibit myogenesis. In addition, PKC is able to phosphorylate myogenin and could be a major mediator of this inhibition.

SUMMARY OF THE INVENTION

The present invention provides nucleic acid molecules coding for ERK-5; ERK-5 polypeptides; recombinant nucleic acid molecules; cells containing the recombinant nucleic acid molecules; antisense ERK-5 nucleic acid constructs; antibodies having binding affinity to an ERK-5 polypeptide; hybridomas containing the antibodies; nucleic acid probes for the detection of ERK-5 nucleic acid; a method of detecting ERK-5 nucleic acid or polypeptide in a sample; kits containing nucleic acid probes or antibodies; a method of detecting a compound capable of binding to ERK-5 or a fragment thereof; a method of detecting an agonist or antagonist of ERK-5 activity; a method of agonizing or antagonizing ERK-5 associated activity in a mammal; a method of treating diabetes mellitus, skeletal muscle diseases, Alzheimer's disease, or peripheral neuropathies in a mammal with an agonist or antagonist of ERK-5 activity; and a pharmaceutical composition comprising an ERK-5 agonist or antagonist.

ERK-5 shows 6% similarity (38% identity) to the human ERK1 peptide sequence, 64% similarity to the rat ERK1 and ERK2 (39% and 37% identity, respectively) and 55% similarity to the rat ERK3 (30% identity). Featured herein are the molecular cloning and characterization of a novel member of the MAP kinase family, termed hERK5, from human skeletal muscle. The gene encodes a protein of 393 amino acids which delivers an apparent molecular weight of 45 kD. It was overexpressed in different eukaryotic cell systems without changing their growth rate. hERK5 can be activated by orthovanadate treatment of overexpressing cells, but not with PCS or growth factors. When overexpressed in the mouse myoblast cell line C2C12, hERK5, in contrast to its kinase negative mutant, increases terminal differentiation after serum withdrawal. These results indicate that hERK5 might play a role in commitment or differentiation of myoblasts, but not, like other members of the MAP kinase family, in cellular growth and proliferation Thus, in one aspect, the present invention provides an isolated, enriched, or purified polypeptide comprising an amino acid sequence corresponding to at least 9 contiguous amino acids of SEQ. ID. NO. 2.

By "isolated" in reference to a polypeptide is meant a polymer of 2 (preferably 9, more preferably 13, most preferably 25) or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is the predominate sequence present (at least 10–20% more than any other sequence) and is essentially free (about 90–95% pure at least) of non-amino acid material naturally associated with it.

By the use of the term "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term significant here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The other source amino acid may, for example, comprise amino acid encoded by a yeast or bacterial genome, or a cloning vector such as pUC19. The term is meant to cover only those situations in which man has intervened to elevate the proportion of the desired amino acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect, the invention provides an organism or cell that contains a recombinant nucleic acid molecule comprising, 5' to 3', a promoter effective to initiate transcription in a host cell and a nucleic acid sequence encoding at least 9 contiguous amino acids of SEQ. ID. NO. 2. The present invention also provides an organism or cell that contains a recombinant nucleic acid molecule comprising a transcriptional region functional in a cell, a sequence complimentary to an RNA sequence encoding at least 9 amino acids of SEQ. ID. NO. 2, and a transcriptional termination region functional in said cell.

In another aspect the invention provides an antibody having a detectably stronger binding affinity to a polypeptide comprising at least 9 contiguous amino acids of SEQ. ID. NO. 2, than to a polypeptide comprising 9 or more contiguous amino acids of ERK-1, ERK-2, ERK-3, or ERK-4. Also provided is a hybridoma which produces such an antibody.

In yet another embodiment the invention features a method of detecting the presence or amount of a polypeptide comprising at least 9 contiguous amino acids of SEQ. ID. NO. 2 in a sample. The method involves contacting said sample with an antibody as described above, under conditions such that immunocomplexes form, and detecting the presence or amount of said antibody bound to said polypeptide.

A diagnostic kit for performing such a method is also provided. The kit contains a first container means containing the antibody as described above, and second container means containing a conjugate comprising a binding partner of said monoclonal antibody and a label.

A method of detecting a compound capable of binding to a polypeptide comprising at least 9 contiguous amino acids of SEQ. ID. NO. 2 is also provided. The method involves the steps of incubating the compound with said polypeptide and detecting the presence of the compound bound to said polypeptide.

A method of detecting an agonist or antagonist of ERK-5 activity comprising incubating cells that produce ERK-5 in the presence of a compound and detecting changes in the level of ERK-5 activity is also provided.

Also featured is a method of agonizing or antagonizing ERK-5 associated activity in a mammal, preferably one with a muscle differentiation disorder, comprising administering to said mammal an agonist or antagonist to ERK-5 in an amount sufficient to effect said agonism or antagonism.

Also provided is a pharmaceutical composition comprising an ERK-5 agonist or antagonist in an amount sufficient to alter ERK-5 associated activity, and a pharmaceutically acceptable diluent, carrier, or excipient.

In another aspect the invention features a method of screening potential agents useful for treatment of a disease or condition characterized by an abnormality in a signal transduction pathway that contains an interaction between a ERK-5 polypeptide and a natural binding partner (NBP). The method involves assaying potential agents for those able to promote or disrupt the interaction as an indication of a useful agent.

By "screening" is meant investigating an organism for the presence or absence of a property. The process may include measuring or detecting various properties, including the level of signal transduction and the level of interaction between a ERK-5 poplypeptide and a NBP.

By "disease or condition" is meant a state in an organism, e.g., a human, which is recognized as abnormal by members of the medical community. The disease or condition may be characterized by an abnormality in one or more signal transduction pathways in a cell, preferably a muscle cell, wherein one of the components of the signal transduction pathway is either a ERK-5 polypeptide or a NBP.

Specific diseases or disorders which might be treated or prevented, based upon the affected cells include muscle cell differentiation disorders such as muscular dystrophies. In preferred embodiments, the methods described herein involve identifying a patient in need of treatment. Those skilled in the art will recognize that various techniques may be used to identify such patients.

By "abnormality" is meant an a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in cell function, viability or differentiation state. We have determined that such abnormality in a pathway can be alleviated by action at the ERK-5:NBP interaction site in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a ERK-5 polypeptide and a NBP, since the complex formed by such interaction is part of the signal transduction pathway. However, the disease or condition may be characterized by an abnormality in the signal transduction pathway even if the level of interaction between the ERK-5 polypeptide and NBP is normal.

By "interact" is meant any physical association between polypeptides, whether covalent or non-covalent. This linkage can include many chemical mechanisms, for instance covalent binding, affinity binding, intercalation, coordinate binding and complexation. Examples of non-covalent bonds include electrostatic bonds, hydrogen bonds, and Van der Waals bonds. Furthermore, the interactions between polypeptides may either be direct or indirect. Thus, the association between two given polypeptides may be achieved with an intermediary agent, or several such agents, that connects the two proteins of interest (e.g., a ERK-5 polypeptide and a NBP). Another example of an indirect interaction is the independent production, stimulation, or inhibition of both a ERK-5 polypeptide and NBP by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the ERK-5 polypeptide relative to the control exercised over the NBP.

By "disrupt" is meant that the interaction between the ERK-5 polypeptide and NBP is reduced either by preventing expression of the ERK-5 polypeptide, or by preventing expression of the NBP, or by specifically preventing interaction of the naturally synthesized proteins or by interfering with the interaction of the proteins.

By "promote" is meant that the interaction between a ERK-5 polypeptide and NBP is increased either by increasing expression of a ERK-5 polypeptide, or by increasing expression of a NBP, or by decreasing the dephosphorylating activity of the corresponding regulatory TP (or other phosphatase acting on other phosphorylated signalling components) by promoting interaction of the ERK-5 polypeptide and NBP or by prolonging the duration of the interaction. Covalent binding can be promoted either by direct condensation of existing side chains or by the incorporation of external bridging molecules. Many bivalent or polyvalent linking agents are useful in coupling polypeptides, such as an antibody, to other molecules. For example, representative coupling agents can include organic compounds such as thioesters, carbodiimides, succinimideesters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, *J. Immunol.* 133:1335–2549; Jansen, F. K., et al., 1982, *Immunological Rev.* 62:185–216; and Vitetta et al., supra).

By "NBP" is meant a natural binding partner of a ERK-5 polypeptide that naturally associates with a ERK-5 polypeptide. The structure (primary, secondary, or tertiary) of the particular natural binding partner will influence the particular type of interaction between the ERK-5 polypeptide and the natural binding partner. For example, if the natural binding partner comprises a sequence of amino acids complementary to the ERK-5 polypeptide, covalent bonding may be a possible interaction. Similarly, other structural characteristics may allow for other corresponding interactions. The interaction is not limited to particular. residues and specifically may involve phosphotyrosine, phosphoserine, or phosphothreonine residues. A broad range of sequences may be capable of interacting with ERK-5 polypeptides. Using techniques well known in the art, one may identify several natural binding partners for ERK-5 polypeptides.

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., Protein Science, 2:1785–1797, 1993) provide possible methods for measuring the amount or intensity of a given signal. Depending upon the particular disease associated with the abnormality in a signal transduction pathway, various symptoms may be detected. Those skilled in the art recognize those symptoms that are associated with the various other diseases described herein. Furthermore, since some adapter molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

In another aspect the invention features a method of diagnosis of an organism for a disease or condition characterized by an abnormality in a signal transduction pathway that contains an interaction between a ERK-5 polypeptide and a NBP. The method involves detecting the level of interaction as an indication of said disease or condition.

By "organism" is meant any living creature. The term includes mammals, and specifically humans. Preferred organisms include mice, as the ability to treat or diagnose mice is often predictive of the ability to function in other organisms such as humans.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between ERK-5 polypeptides and NBPs may form the basis to define and diagnose a newly named disease or condition. For example, conventional cancers are classified according to the presence of a particular set of symptoms. However, a subset of these symptoms may both be associated with an abnormality in a particular signalling pathway, such as the ras[21] pathway and in the future these diseases may be reclassified as ras[21] pathway diseases regardless of the particular symptoms observed.

Yet another aspect of the invention features a method for treatment of an organism having a disease or condition characterized by an abnormality in a signal transduction pathway. The signal transduction pathway contains an interaction between a ERK-5 polypeptide and a NBP and the method involves promoting or disrupting the interaction, including methods that target the ERK-5:NBP interaction directly, as well as methods that target other points along the pathway.

In preferred embodiments the disease or condition which is diagnosed or treated are those described above, the agent is a dominant negative mutant protein provided by gene therapy or other equivalent methods as described below and the agents is therapeutically effective and has an $EC_{50}$ or $IC_{50}$ as described below.

By "dominant negative mutant protein" is meant a mutant protein that interferes with the normal signal transduction pathway. The dominant negative mutant protein contains the domain of interest (e.g., an ERK-5 polypeptide or a NBP), but has a mutation preventing proper signaling, for example by preventing binding of a second domain from the same protein. One example of a dominant negative protein is described in Millauer et al., Nature Feb. 10, 1994. The agent is preferably a peptide which blocks or promotes interaction of the ERK-5 polypeptide and the NBP. The peptide may be recombinant, purified, or placed in a pharmaceutically acceptable carrier or diluent.

An $EC_{50}$ or $IC_{50}$ of less than or equal to 100 $\mu$M is preferable, and even more preferably less than or equal to 50 $\mu$M, and most preferably less that or equal to 20 $\mu$M. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. In addition, the molecule may have an $EC_{50}$ or $IC_{50}$ less than or equal to 100 $\mu$M at a muscle cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 $\mu$mole of the molecule, depending on its $EC_{50}$ or $IC_{50}$ and on the age and size of the patient, and the disease associated with the patient.

Further objects and advantages of the present invention will be clear from the description that follows.

BRIEF DESCRIPTION OF THE DRAWINGS

FIGS. 1a–1c show the full length nucleotide (SEQ ID NO: 1) and amino acid sequence (SEQ ID NO:2 of hERK5.

FIGS. 2a–2b compare the amino acid sequence of hERK5 TO hERK1, hERK2, and hERK3.

DESCRIPTION OF THE PREFERRED EMBODIMENTS

The present invention features the cDNA cloning and functional characterization of a novel member of the MAP kinase family which we termed hERK5 . The amino acid sequence shows about 60% similarity to human ERK1, 2 and 3, respectively. In addition to the conserved residues of protein kinases, the catalytically important residues of MAP kinases, the lysine residue within the VAIKK(SEQ ID. NO:11) motif (amino acid position 56 of hERK5) and the regulatory phosphorylation sites in subdomain VIII (threonine 183 and tyrosine 185) are conserved in the novel protein sequence as well.

To generate an inactive form of hERK5, we mutated the tyrosine residue at position 185 as one of the sites which are involved in activation of MAP kinases by phosphorylation to phenylalanine. As shown in the MBP phosphorylation assay after transient expression in 293 cells, this mutant is indeed kinase negative. It was thus used as negative control to investigate the biological function of hERK5.

There exist diverse forms of hERK5, including a doublet of 44/46 kD representing unphosphorylated and phosphorylated protein, respectively, and a band of about 56 kD which seems to change to a doublet of 55/57 kD in the Y185F mutant of hERK5 and which shows a higher MBP kinase activity than the 44/46 kD doublet. The identity of the 56 kD band which is specifically recognized by antisera both against native as well as denatured hERK5 protein independently of stimulation or starvation of 293 cells for serum or growth factors can not be finally determined. The fuzzy shape of the 56 kD band indicates some kind of phosphorylation. Indeed, the 56 kD as well as the 46 kD band show a signal in the αPY-blot of total lysates of 293 cells transfected with hERK5 wt cDNA, whereas none of the bands expressed after transfection with Y185F DNA is tyrosine phosphorylated. The intensity of the 56 kD and in comparison to the 44/46 kD doublet differs between the transient overexpression system of 293 cells and stably expressing NIH3T3 or C2C12 cells. In 293 cells, the 56 kD band is as prominent as the lower two bands (both in immunoprecipitation and Western Blot), whereas in NIH3T3 or C2C12 cells, the upper band is hardly visible in immunoprecipitates and could not be detected in the Western Blot. Thus, the appearance of the 56 kD band might be correlated to the high amount of overexpressed protein in 293 cells and could represent an ubiquitinated form of hERK5.

In order to investigate the signalling pathways involved in activation of hERK5, we overexpressed hERK5 wt and Y185F mutant, respectively, either transiently in 293 cells together with the human insulin receptor (A-type) or as stable NIH3T3/C2C12 lines. Starved cells were either ligand stimulated (293 cells) or treated with different agents known to induce MAP kinase activity, lysed and analysed for electrophoretic mobility shift of hERK5 and ERK1/2 due to phosphorylation and thereby activation.

The phosphorylation and thus activation status of hERK5 in transfected 293 cells is not changed upon insulin treatment, meaning that either the high level of protein expression is interfering with starvation or activation of hERK5 or that insulin does not stimulate hERK5 activity. However, the Western Blots of stably overexpressing NIH3T3 and C2C12 cells after treatment with orthovanadate, TPA, ocadaic acid, insulin or FCs clearly demonstrate that hERK5 is not activated via the same pathways as are ERK1 and 2 in these cell systems. Phosphorylation of hERK5 wt could only be induced by treatment of cells with orthovanadate for 2 h, but not with insulin, TPA or FCS. This result indicates the existence of a phosphotyrosine-phosphatase that is able to dephosphorylate hERK5 in NIH3T3/C2C12 cells. Activation of hERK5 might be caused by autophosphorylation (as described for ERK1 and 2) or phosphorylation via a (specific) MAP kinase kinase in a mitogen-nonresponsive or contraresponsive way.

Since hERK5 appeared to be strongly expressed in skeletal muscle, we decided to examine the influence of hERK5 on myoblast differentiation. Therefore, we retrovirally infected C2C12 cells to stably overexpress hERK5 wt and Y185F, respectively, and grew the cells in differentiation medium. We could observe a clear stimulation of myoblast fusion in hERK5 wt expressing cells compared to mock infected C2C12 cells. Furthermore, the kinase negative form of hERK5 strongly reduced myotube formation in comparison to mock infected cells. These results together with the data obtained in stably expressing NIH3T3/C2C12 cells indicate that hERK5 might play a role rather in cellular differentiation than in proliferation. A further support of this hypothesis has been obtained by MTT growth assays of stably overexpressing NIH3T3/C2C12 cell in different FCS concentrations where no difference in growth rate could be observed among wt hERK5, Y185F or mock infected cells.

However, the molecular function of hERK5 could involve similar mechanisms as those of ERK1 and 2 which phosphorylate transcription factors in response to mitogens. Upon activation, hERK5 might phosphorylate and activate muscle specific transcription factors that are either constitutively expressed or whose expression is transcriptionally regulated during differentiation and thus contribute to commit myoblasts for differentiation.

I. Substantially Pure ERK-5 Polypeptides

In another embodiment, the present invention relates to a substantially pure polypeptide having an amino acid sequence corresponding to ERK-5, or at least 9 contiguous amino acids thereof (preferably, at least 10, 15,20, or 30 contiguous amino acids thereof). In a preferred embodiment, the polypeptide has the amino acid sequence set forth in SEQ ID NO:2, or mutant or species variation thereof, or at least 9 contiguous amino acids thereof (preferably, at least 10, 15, 20, or 30 contiguous amino acids thereof).

A variety of methodologies known in the art can be utilized to obtain the peptide of the present invention. In one embodiment, the peptide is purified from tissues or cells which naturally produce the peptide. Alternatively, the above-described isolated nucleic acid fragments could be used to expressed the ERK-5 protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

II. A Method of Detecting the Presence of ERK-5 in a Sample

In another embodiment, the present invention relates to a method of detecting the presence of ERK-5 in a sample comprising a) contacting said sample with the above-described nucleic acid probe, under conditions such that hybridization occurs, and b) detecting the presence of said probe bound to said nucleic acid molecule. One skilled in the art would select the nucleic acid probe according to techniques known in the an as described above. Samples to be tested include but should not be limited to RNA samples of human tissue.

ERK-5 has been found to be predominantly expressed in muscle. Accordingly, ERK-5 probes may be used detect the presence of RNA from muscle in a sample. Further, altered expression levels of ERK-5 RNA in an individual, as compared to normal levels, may indicate the presence of muscular disease or diabetes mellitus. The ERK-5 probes may further be used to assay cellular factor activity in general and specifically in muscle tissue.

III. A Kit for Detecting the Presence of ERK-5 in a Sample

In another embodiment, the present invention relates to a kit for detecting the presence of ERK-5 in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline, phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and-the like), and containers which contain the reagents used to detect the hybridized probe, bound antibody amplified product, or the like.

One skilled in the art will readily recognize that the nucleic acid probes described in the present invention can readily be incorporated into one of the established kit formats which are well known in the art.

IV. DNA Constructs Comprising a ERK-5 Nucleic Acid Molecule and Cells Containing These Constructs In another embodiment, the present invention relates to a cell or organism that contains a recombinant nucleic acid molecule described below.

In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecules.

In another embodiment, the present invention relates to a nucleic acid molecule comprising a transcriptional region functional in a cell, a sequence complimentary to an RNA sequence encoding an amino acid sequence corresponding to the above-described polypeptide, and a transcriptional termination region functional in said cell.

As used herein, a cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an ERK-5 gene may be obtained by the above-described methods. This region may be retained for its transcriptional termination regulatory sequences, such as termination and polyadenylation. Thus, by retaining the 3'-region naturally contiguous to the DNA sequence encoding an ERK-5 gene, the transcriptional termination signals may be provided. Where the transcriptional termination signals are not satisfactorily functional in the expression host cell, then a 3' region functional in the host cell may be substituted.

Two DNA sequences (such as a promoter region sequence and an ERK-5 sequence) are said to be operably linked if the nature of the linkage between the two DNA sequences does not (1) result in the introduction of a frame-shift mutation, (2) interfere with the ability of the promoter region sequence to direct the transcription of an ERK-5 gene sequence, or (3) interfere with the ability of the an ERK-5 gene sequence to be transcribed by the promoter region sequence. Thus, a promoter region would be operably linked to a DNA sequence if the promoter were capable of effecting transcription of that DNA sequence.

Thus, to express an ERK-5 gene, transcriptional and translational signals recognized by an appropriate host are necessary. The present invention encompasses the expression of the ERK-5 gene (or a functional derivative thereof) in either prokaryotic or eukaryotic cells. Prokaryotic hosts are, generally, very efficient and convenient for the production of recombinant proteins and are, therefore, one type of preferred expression system for the ERK-5 gene.

Prokaryotes most frequently are represented by various strains of E. coli. However, other microbial-strains may also be used, including other bacterial strains. In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

Recognized prokaryotic hosts include bacteria such as E. coil, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express ERK-5 (or a functional derivative thereof) in a prokaryotic cell, it is necessary to operably link the ERK-5 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage. λ ($P_L$ and $P_R$), the trp, recA, lacZ, lacI, and gal promoters of E. coli, the α-amylase (Ulmanen et at., J. Bacteriol. 162:176–182 (1985)) and the ς-28-specific promoters of B. subtilis (Gilman et at., Gene sequence 32:11–20(1984)), the promoters of the bacteriophages of Bacillus (Gryczan, In: The Molecular Biology of the Bacilli, Academic Press, Inc., NY (1982)), and Streptomyces promoters (Ward et at., Mol. Gen. Genet. 203:468–478(1986)).

Prokaryotic promoters are reviewed by Glick (J. Ind. Microbiot. 1:277–282(1987)); Cenatiempo (Biochimie 68:505–516(1986)); and Gottesman (Ann. Rev. Genet. 18:415–442 (1984)). Proper expression in a prokaryotic cell also requires the presence of a ribosome binding site upstream of the gene sequence-encoding sequence. Such ribosome binding sites are disclosed, for example, by Gold et at. (Ann. Rev. Microbial. 35:365–404(1981)).

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the ERK-5 peptide of interest. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences.

Another preferred host is an insect cell, for example the Drosophila larvae. Using insect cells as hosts, the Drosophila alcohol dehydrogenase promoter can be used. Rubin, Science 240:1453–1459(1988). Alternatively, baculovirus vectors can be engineered to express large amounts of ERK-5 in insects cells (Jasny, Science 238:1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of ERK-5.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated of interest are regulatory signals which are temperature-sensitive so that by varying the temperature, expression can be repressed or initiated, or are subject to chemical (such as metabolite) regulation.

As discussed above, expression of ERK-5 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et, al., J. Mol. Appl. Gen. 1:273–288(1982)); the TK promoter of Herpes virus (McKnight, Cell 31:355–365 (1982)); the SV40 early promoter (Benoist et al., Nature (London) 290:304–310(1981)); the yeast gal4 gene sequence promoter (Johnston et al., Proc. Natl. Acad. Sci. (USA). 79:6971–6975(1982); Silver et al., Proc. Natl. Acad. Sci. (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes ERK-5 (or a functional derivative thereof) does not contain any intervening codons which are capable of encoding a methionine (i.e., AUG). The presence of such codons results either in a formation of a fusion protein (if the AUG codon is in the same reading frame as the ERK-5 coding sequence) or a frame-shift mutation (if the AUG codon is not in the same reading frame as the ERK-5 coding sequence).

An ERK-5 nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Molec. Cell. Biol. 3:280(1983).

In a preferred embodiment, the introduced nucleic acid molecule will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in E. coil (such as, for example, pBR322, ColEl, pSC101, pACYC 184, πVX. Such plasmids are, for example, disclosed by Sambrook (cf. Molecular Cloning: A Laboratory Manual, second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacitli, Academic Press, NY (1982), pp. 307–329). Suitable Streptomyces plasmids include p1J101 (Kendall et al., J. Bacteriol. 169:4177–4183 (1987)), and streptomyces bacteriophages such as φC31 (Chater et al., In: Sixth International Symposium on Actinomycetales Biology, Akademiai Kaido, Budapest, Hungary (1986), pp. 45–54). Pseudomonas plasmids are reviewed by John et al. (Rev. Infect. Dis. 8:693–704(1986)), and Izaki (Jpn. J. Bacteriol. 33:729–742 (1978)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274(1982); Broach, In: The Molecular Biology of the Yeast Saccharomyces: Life Cycle and Inheritance, Cold Spring Harbor Laboratory, Cold Spring Harbor, N.Y., p. 445–470 (1981); Broach, Cell 28:203–204 (1982); Bollon et at., J. Ctin. Hematol. Oncol. 10:39–48 (1980); Maniatis, In: Cell Biology: A Comprehensive Treatise, Vol. 3, Gene Sequence Expression, Academic Press, NY, pp. 563–608(1980).

Once the vector or nucleic acid molecule containing the construct(s) has been prepared for expression, the DNA construct (s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of ERK-5 or fragments thereof. This can take place in the transformed cells as such, or following the induction of these cells to differentiate (for example, by administration of bromodeoxyuracil to neuroblastoma cells or the like).

A variety of incubation conditions can be used to form the peptide of the present invention. The most preferred conditions are those which mimic physiological conditions.

V. An Antibody Having Binding Affinity to an ERK-5 Polypeptide or a Binding Fragment Thereof and a Hybridoma Containing the Antibody In another embodiment, the present invention relates to an antibody having binding affinity to an ERK-5 polypeptide, or a binding fragment thereof. In a preferred embodiment, the polypeptide has the amino acid sequence set forth in SEQ ID NO:2, or mutant or species variation thereof, or at least 9 contiguous amino acids thereof (preferably, at least 10, 15, 20, or 30 contiguous amino acids thereof).

In another preferred embodiment, the present invention relates to an antibody having binding affinity to an ERK-5 polypeptide, or a binding fragment thereof and not to ERK-1, ERK-2, ERK-3, or ERK-4. Such an antibody may be isolated by comparing its binding affinity to ERK-5 with its binding affinity to ERK-1, ERK-2, ERK-3, or ERK-4. Those which bind selectively to ERK-5 would be chosen for use in methods requiring a distinction between ERK-5 and ERK-1, ERK-2, ERK3, or ERK-4 polypeptides. Such methods could include, but should not be limited to, the analysis of altered ERK-5 expression in tissue containing ERK-1, ERK-2, ERK-3, or ERK-4.

The ERK-5 proteins of the present invention can be used in a variety of procedures and methods, such as for the generation of antibodies, for use in identifying pharmaceutical compositions, and for studying DNA/protein interaction. The ERK-5 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

In another embodiment, the present invention relates to a hybridoma which produces the above-described monoclonal antibody, or binding fragment thereof. A hybridoma is an immortalized cell line which is capable of secreting a specific monoclonal antibody. In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21(1980)).

Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization. For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124(1988)).

Hybridomas secreting the desired antibodies are cloned and the class and subclass is determined using procedures known in the art (Campbell, Monoclonal Antibody Technology: Laboratory Techniques in Biochemistry and Molecular Biology, supra (1984)). For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., J. Histochem, Cytochem. 18:315(1970); Bayer et at., Meth. Enzym. 62:308(1979); Engval et al., Immunot. 109:129 (1972); Goding, J. Immunol. Meth. 13:215(1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England,. Chapter 10(1986); Jacoby et al., Meth. Enzym. 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W. H. Freeman, NY, pp. 289–307 (1992), and Kaspczak et al., Biochemistry 28:9230–8 (1989).

Anti-peptide peptides can be generated in one of two fashions. First, the anti-peptide peptides can be generated by replacing the basic amino acid residues found in the ERK-5 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VI. A Method of Detecting an ERK-5 Polypeptide in a Sample

In another embodiment, the present invention relates to a method of detecting an ERK-5 polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample. Altered levels of ERK-5 in a sample as compared to normal levels may indicate muscular disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

VII. A Diagnostic Kit Comprising Antibodies to ERK-5

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

VIII. Isolation of Compounds Which Interact With ERK-5

In another embodiment, the present invention relates to a method of detecting a compound capable of binding to ERK-5 or a fragment thereof comprising incubating the compound with ERK-5 or fragment thereof and detecting the presence of the compound bound to ERK-5 or fragment thereof. In a preferred embodiment, the compound is present within a complex mixture, for example, serum, body fluid, or cell extracts.

In another embodiment, the present invention relates to a method of detecting an agonist or antagonist of ERK-5 activity comprising incubating cells that produce ERK-5 in the presence of a compound and detecting changes in the level of ERK5 activity. The compounds thus identified would produce a change in activity indicative of the presence of the compound. In a preferred embodiment, the compound is present within a complex mixture, for example, serum, body fluid, or cell extracts. Once the compound is identified it can be isolated using techniques well known in the art.

In a further embodiment, the present invention relates to a method of agonizing (stimulating) or antagonizing ERK-5 associated activity in a mammal comprising administering to said mammal an agonist or antagonist to ERK-5 in an amount sufficient to effect said agonism or antagonism. In a preferred embodiment, the present invention relates to a method of treating diabetes mellitus, skeletal muscle diseases, Alzheimer's disease, or peripheral neuropathies in a mammal with an agonist or antagonist of ERK-5 activity comprising administering the agonist or antagonist to a mammal in an amount sufficient to agonize or antagonize ERK-5 associated functions. Further, 'since ERK-5 is preferentially expressed in skeletal muscle, the agonist or antagonist might be used in normal individuals.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg, preferably 0.1 mg/kg to 1.0 mg/kg, of the agonist or antagonist of the invention, in one or more administrations daily, for one or several days. The agonist or antagonist can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, antioxidants, chelating agents, inert gases and the like. See, generally, Remington's Pharmaceutical Science, 16th Ed., Mack Eds. (1980).

In another embodiment, the present invention relates to a pharmaceutical composition comprising the above described ERX-5 agonist or antagonist in an amount sufficient to alter ERK-5 associated activity, and a pharmaceutically acceptable diluent, carrier, or excipient. Appropriate concentrations and dosage unit sizes can be readily determined by one skilled in the art as described above (See, for example, Remington's Pharmaceutical Sciences (16th ed., Osol, A., Ed., Mack, Easton Pa. (1980) and WO 91/19008).

IX. Compositions

The present invention relates to removing or reducing an abnormality in a signal transduction pathway, wherein the signal transduction pathway contains a ERK5 polypeptide. The present invention also relates to compositions and methods for the treatment of disorders which involve modulating the activity and/or level of individual components, and relates to methods for the identification of agents for such treatments. Additionally, the present invention relates to methods and compositions for prognostic evaluation of such disorders.

Described herein are compositions and methods for the prevention, prognostic evaluation, and treatment of disorders described herein, preferably cell proliferative disorders and hematopoietic cell disorders, in which a ERK5 polypeptide may be involved.

First, methods and compositions for the treatment of such disorders are described. Such methods and compositions may include, but are not limited to the agents capable of decreasing or inhibiting the interaction between a ERK5 polypeptide and a ERK5 polypeptide binding partner and agents capable of inhibiting or decreasing the activity of such complexes, agents capable of modulating the activity and/or level of individual components of the proteins, and the use and administration of such agents. Agents capable of modulating the activity and/or level of interaction between a ERK5 polypeptide and a ERK5 polypeptide binding partner include those agents that inhibit or decrease the dephosphorylating activity of tyrosine phosphatases.

Second, methods are described for the identification of such agents. These methods may include, for example, assays to identify agents capable of disrupting or inhibiting or promoting the interaction between components of the complexes (e.g., ERK5:NBP complexes), and may also include paradigms and strategies for the rational design of drugs capable of disruption and/or inhibition and/or promotion of such complexes.

The complexes involved in the invention include a ERK5 polypeptide and a NBP or derivatives thereof, as described below. Under standard physiological conditions, the components of such complexes are capable of forming stable, non-covalent attachments with one or more of the other complex components. Methods for the purification and production of such protein complexes, and of cells that exhibit such complexes are described below.

X. Disruption of Protein Complexes

Disruption of complexes (e.g., ERK5:NBP complexes), for example by decreasing or inhibiting the interactions between component members of such a complex may have differing modulatory effects on the event involved, depending on the individual protein complex. "Disruption", as used here, is meant to refer not only to a physical separation of protein complex components, but also refers to a perturbation of the activity of the complexes, regardless of whether or not such complexes remain able, physically, to form. "Activity", as used here, refers to the function of the protein complex in the signal transduction cascade of the cell in which such a complex is formed, i.e., refers to the function of the complex in effecting or inhibiting a transduction of an extracellular signal into a cell. For example, the effect of complex disruption may augment, reduce, or block a signal normally transduced into the cell. Likewise, depending on the disorder involved, either augmentation, reduction, or blockage of a signal normally transduced into the cell will be desirable for the treatment of the disorder.

A disorder involving a complex may, for example, develop because the presence of such a complex brings about the aberrant inhibition of a normal signal transduction event. In such a case, the disruption of the complex would allow the restoration of the usual signal transduction event.

Further, an aberrant complex may bring about an altered subcellular adapter protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Nucleotide sequences encoding peptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, *Molecular Cloning: A Laboratory Manual*, Cold Spring Harbor Laboratory, N.Y. and in Ausubel et al., *Current Protocols in Molecular Biology*, Greene Publishing Associates and Wiley Interscience, N.Y, 1989. Complex-binding domains can be identified using, for example, techniques such as those described in Rotin et al. (Rotin et al., *EMBO J*. 11:559–567, 1992), Songyang et al. (Songyang et al., *Cell* 72:767–778, 1993), Felder et al., *Mol. Cell. Biol.* 13:1449–1455, 1993), Fantl et al. (*Cell* 69:413–422, 1992), and Domchek et al. (*Biochemistry* 31:9865–9870, 1992).

Alternatively, antibodies capable of interfering with complex formation may be produced as described below and administered for the treatment of disorders involving a component capable of forming a complex with another protein. Alternatively, nucleotide sequences encoding single-chain antibodies may be expressed within the target cell population by utilizing, for example, techniques such as those described in Marasco et al. (Marasco et al., *Proc. Natl. Acad. Sci. USA* 90:7889–7893, 1993). Agents which act intracellularly to interfere with the formation and/or activity of the protein complexes of the invention may also be small organic or inorganic compounds. A method for identifying these and other intracellular agents is described below.

XI. Antibodies to Complexes

Described herein are methods for the production of antibodies which are capable of specifically recognizing a complex or an epitope thereof, or of specifically recognizing an epitope on either of the components of the complex, especially those epitopes which would not be recognized by the antibody when the component is present separate and apart from the complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a complex in a biological sample, or, alternatively, as a method for the inhibition of a complex formation, thus inhibiting the development of a disorder. In general, the techniques described above regarding antibodies to ERK-5 may also be used in relation to antibodies to the complex and vice versa.

Polyclonal antibodies are heterogeneous populations of antibody molecules derived from the sera of animals immunized with an antigen, such as a complex, or an antigenic functional derivative thereof. For the production of polyclonal antibodies, various host animals may be immunized by injection with the complex including but not limited to rabbits, mice, rats, etc. Various adjuvants may be used to increase the immunological response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler and Milstein (*Nature* 256:495–497, 1975) and U.S. Pat. No. 4,376,110), the human B-cell hybridoma technique (Kosbor et al., *Immunology Today* 4:72, 1983; Cole et al., *Proc. Natl. Acad. Sci. USA* 80:2026–2030, 1983), and the EBV-hybridoma technique (Cole et al., *Monoclonal Antibodies And Cancer Therapy*, Alan R. Liss, Inc., 1985, pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci.*, 81:6851–6855, 1984; Neuberger et al., *Nature*, 312:604–608, 1984; Takeda et al., *Nature*, 314:452–454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–426, 1988; Huston et al., *Proc. Natl. Acad. Sci. USA* 85:5879–5883, 1988; and Ward et al., *Nature* 334:544–546, 1989) can be adapted to produce complex-specific single chain antibodies. Single chain antibodies are formed by linking the heavy and light chain fragment of the Fv region via an amino acid bridge, resulting in a single chain polypeptide.

Antibody fragments which contain specific binding sites of a complex may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, *Science*, 246:1275–1281) to allow rapid and easy identification of monoclonal Fab fragments with the desired specificity to the PTK/adapter complex.

One or more components of a protein complex may be present at a higher than normal cellular level (i.e., higher than the concentration known to usually be present in the cell type exhibiting the protein complex of interest) and/or may exhibit an abnormally increased level of cellular activity (i.e., greater than the activity known to usually be present in the cell type exhibiting the protein complex of interest).

For example, the gene encoding a protein complex component may begin to be overexpressed, or may be amplified (i.e., its gene copy number may be increased) in certain cells, leading to an increased number of component molecules within these cells. Additionally, a gene encoding a protein complex component may begin to express a modified protein product that exhibits a greater than normal level of activity. "Activity", here, refers to the normal cellular function of the component, either enzymatic or structural whose function may include, for example, bringing two or more cellular molecules into the appropriate proximity.

Such an increase in the cellular level and/or activity of a protein complex may lead to the development of a disorder. Treatment of such disorders may, therefore, be effectuated by the administration of agents which decrease the cellular level and/or the activity of the overexpressed and/or overactive protein complex component. Techniques for decreasing the cellular level and/or the activity of one or more of the protein complex components of interest may include, but are not limited to antisense or ribozyme approaches, and/or gene therapy approaches, each of which is well known to those of skill in the art.

XII. Antisense and Ribozyme Approaches

Included in the scope of the invention are oligoribonucleotides, including antisense RNA and DNA molecules and ribozymes that function to inhibit translation of one or more components of a protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569.

Both anti-sense RNA and DNA molecules and ribozymes of the invention may be prepared by any method known in the art for the synthesis of RNA molecules. See, Draper, id. hereby incorporated by reference herein. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

XIII. Gene Therapy

ERK5 or its genetic sequences will also be useful in gene therapy (reviewed in Miller, Nature 357:455–460, (1992). Miller states that advances have resulted in practical approaches to human gene therapy that have demonstrated positive initial results. An in vivo model of gene therapy for human severe combined immunodeficiency is described in Ferrari, et al., Science 251:1363–1366, (1991). The basic science of gene therapy is described in Mulligan, Science 260:926–931, (1993).

In one preferred embodiment, an expression vector containing the ERK5 coding sequence is inserted into cells, the cells are grown in vitro and then infused in large numbers into patients. In another preferred embodiment, a DNA segment containing a promoter of choice (for example a strong promoter) is transferred into cells containing an endogenous ERK5 in such a manner that the promoter segment enhances expression of the endogenous ERK5 gene (for example, the promoter segment is transferred to the cell such that it becomes directly linked to the endogenous ERK5 gene).

The gene therapy may involve the use of an adenovirus containing ERK5 cDNA targeted to a tumor, systemic ERK5 increase by implantation of engineered cells, injection with ERK5 virus, or injection of naked ERK5 DNA into appropriate tissues.

Target cell populations (e.g., muscle cells) may be modified by introducing altered forms of ERK5 in order to modulate the activity of such cells. For example by reducing or inhibiting an a nerve cell within target cells, an abnormal response leading to a condition may be decreased, inhibited, or reversed. Deletion or missense mutants of ERK5, that retain the ability to interact with other components of the nervous system but cannot participate in normal function may be used to inhibit an abnormal, deleterious response.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant ERK5 protein into the targeted cell population (e.g., tumor cells). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Feigner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi MR, *Cell* 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.*, 15:1311–26 (1987)); lipofection/liposome fusion, wherein DNA is packaged into lipophilic vesicles which fuse with a target cell (Felgner P L., et al., *Proc. Natl. Acad. Sci. USA.* 84:7413–7 (1987)); and particle bombardment using DNA bound to small projectiles (Yang N S. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., *Am. J. Respir. Cell. Mol. Biol.*, 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding ERK5 is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set-forth. "Gene replacement" as used herein means supplying a nucleic acid sequence which is capable of being expressed in vivo in an animal and thereby providing or augmenting the function of an endogenous gene which is missing or defective in the animal.

XIV. Pharmaceutical Formulations and Modes of Administration

The particular compound, antibody, antisense or ribozyme molecule that affects the protein complexes and the disorder of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics,* 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such; as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means -of conventional mixing, dissolving, granulating, dragee-making, levitating, emulsifying, encapsulating, entrapping or lyophilizing processes.

Pharmaceutical formulations for parenteral administration include aqueous'solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

A ERK5 nucleic acid sequence may be administered utilizing an ex vivo approach whereby cells are removed from an animal, transduced with the ERK5 nucleic acid sequence and reimplanted into the animal. The liver can be accessed by an ex vivo approach by removing hepatocytes from an animal, transducing the hepatocytes in vitro with the ERK5 nucleic acid sequence and reimplanting them into the animal (e.g., as described for rabbits by Chowdhury et al, *Science* 254: 1802–1805, 1991, or in humans by Wilson, *Hum. Gene Ther. 3: 179–222, 1992*) incorporated herein by reference.

Many nonviral techniques for the delivery of a ERK5 nucleic acid sequence into a cell can be used, including direct naked DNA uptake (e.g., Wolff et al., *Science* 247: 1465–1468, 1990), receptor-mediated DNA uptake, e.g., using DNA coupled to asialoorosomucoid which is taken up by the asialoglycoprotein receptor in the liver (Wu and Wu, *J. Biol. Chem.* 262: 4429–4432, 1987; Wu et al., *J. Biol. Chem.* 266: 14338–14342, 1991), and liposome-mediated delivery (e.g., Kaneda et al., *Expt. Cell Res.* 173: 56–69, 1987; Kaneda et al., *Science* 243: 375–378, 1989; Zhu et al., *Science* 261: 209–211, 1993). Many of these physical methods can be combined with one another and with viral techniques; enhancement of receptor-mediated DNA uptake can be effected, for example, by combining its use with adenovirus (Curiel et al., *Proc. Natl. Acad. Sci. USA* 88: 8850–8854, 1991; Cristiano et al., *Proc. Natl. Acad. Sci. USA* 90: 2122–2126, 1993).

The ERK5 or nucleic acid encoding ERK5 may also be administered via an implanted device that provides a support for growing cells. Thus, the cells may remain in the implanted device and still provide the useful and therapeutic agents of the present invention.

XV. Identification of Agents

The complexes, components of such complexes, functional equivalents thereof, and/or cell lines that express such components and exhibit such protein complexes may be used to screen for additional compounds, antibodies, or other molecules capable of modulating the signal transduction event such complexes are involved in. Methods for purifying and/or producing such complexes, components of the complexes, functional equivalents thereof, and/or cell lines are described herein. The compounds, antibodies, or other molecules identified may, for example, act to disrupt the protein complexes of the invention (i.e., decrease or inhibit interactions between component members of the complexes, thereby causing physical separation of the components, and/or perturbing the activity of the complexes) or may lower the cellular level and/or decrease the activity of one or more of the components of such complexes.

Such compounds may include, but are not limited to, peptides made of D- and/or L-configuration amino acids (in, for example, the form of random peptide libraries; see Lam et al., *Nature 354:82–84, 1991*), phosphopeptides (in, for example, the form of random or partially degenerate, directed phosphopeptide libraries, see Songyang et al., *Cell* 767–778, 1993), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments, as described herein.

Compounds that bind to individual components, or functional portions of the individual components of the complexes (and may additionally be capable of disrupting complex formation) may be identified.

One such method included within the scope of the invention is a method for identifying an agent to be tested for an ability to modulate a signal transduction pathway disorder. The method involves exposing at least one agent to a protein comprising a functional portion of a member of the protein complex for a time sufficient to allow binding of the agent to the functional portion of the member; removing non-bound agents; and determining the presence of the compound bound to the functional portion of the member of the protein complex, thereby identifying an agent to be tested for an ability to modulate a disorder involving a polypeptide complex.

By "signal transduction disorder" is meant any disease or condition associated with an abnormality in a signal transduction pathway. The protein complex referred to below is a physical association of dynamin and a ERK5 polypeptide. The level of interaction between the two components of the complex may be abnormal and thus cause the abnormality in the signal transduction pathway. Alternatively, the level of interaction between the complex components may be normal, but affecting that interaction may effectively treat a signal transduction pathway disorder.

The term "protein" refers to a compound formed of 5–50 or more amino acids joined together by peptide bonds. An "amino acid" is a subunit that is polymerized to form proteins and there are twenty amino acids that are universally found in proteins. The general formula for an amino acid is $H_2N-CHR-COOH$, in which the R group can be anything from a hydrogen atom (as in the amino acid glycine) to a complex ring (as in the amino acid tryptophan).

A functional portion of an individual component of the complexes may be defined here as a protein portion of an individual component of a complex still capable of forming a stable complex with another member of the complex under standard cellular and physiological conditions. For example, a functional portion of a component may include, but is not limited to, a protein portion of dynamin which is still capable of stably binding a corresponding ERK5 polypeptide of an associated protein, and thus is still capable of forming a complex with that protein. Further, in the case of the catalytic domains of the individual components of the invention, a functional portion of a catalytic domain may refer to a protein still capable of stably binding a substrate molecule under standard physiological conditions.

One method utilizing this approach that may be pursued in the isolation of such complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. Attachment to said solid support may be direct or by means of a component specific antibody bound directly to the solid support. After incubation, unbound compounds are washed away, component-bound compounds are recovered. By utilizing this procedure, large numbers of types of molecules may be simultaneously screened for complex component-binding activity.

The complex components which may be utilized in the above screening method may include, but are not limited to, molecules or functional portions thereof, such as catalytic domains, phosphorylation domains, extracellular domains, or portions of extracellular domains, such as ligand-binding domains, and adaptor proteins, or functional portions thereof. The peptides used may be phosphorylated, e.g., may contain at least one phosphorylated amino acid residue, preferably a phosphorylated Tyr amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific protein.

Molecules exhibiting binding activity may be further screened for an ability to disrupt protein complexes. Alternatively, molecules may be directly screened for an ability to promote the complexes. For example, in vitro complex formation may be assayed by, first, immobilizing one component, or a functional portion-thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound. In addition, one could look for an increase in binding.

Additionally, complex formation in a whole cell may be assayed by utilizing co-immunoprecipitation techniques well known to those of skill in the art. Briefly, a cell line capable of forming a complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

A preferred method for assessing modulation of complex formation within a cell utilizes a method similar to that described above. Briefly, a cell line capable of forming a complex of interest is exposed to a test compound. The cells are lysed and the lysate contacted with an antibody specific to one component of the complex, said antibody having been previously bound to a solid support. Unbound material is washed away, and the bound material is exposed to a second antibody, said second antibody binding specifically to a second component of the complex. The amount of second antibody bound is easily detected by techniques well known in the art. Cells exposed to an inhibitory test compound will have formed a lesser amount of complex compared to cells not exposed to the test compound, as measured by the amount of second antibody bound. Cells exposed to a test compound that promotes complex formation will have an increased amount of second antibody bound.

The effect of an agent on the differentiation capability of the complex of interest may be directly assayed. Such agents may, but are not required to, include those agents identified by utilizing the above screening technique. For example, an agent or agents may be administered to a cell such as a neuronal cell, capable of forming a complex, for example, which, in the absence of any agent, would not lead to the cell's differentiation. The differentiation state of the cell may then be measured either in vitro or in vivo. One method of measurement may involve observing the amount of neurile growth present.

Agents capable of disrupting complex formation and capable of reducing or inhibiting disorders, which involve the formation of such complexes, or which involve the lack of formation of such complexes, may be used in the treatment of patients exhibiting or at risk for such disorders. A sufficient amount of agent or agents such as those described above may be administered to a patient so that the symptoms of the disease or condition are reduced or eliminated.

XVI. Purification and Production of Complexes

Described in this Section are methods for the synthesis or recombinant expression of components, or fragments thereof, of the protein complexes of the invention. Also described herein are methods by which cells exhibiting the protein complexes of the invention may be engineered.

The complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the complex to a combination of standard methods, for example, ammonium sulfate precipitation, molecular sieve chromatography, and/or ion exchange chromatography.

Alternatively, or additionally, a complex may be purified by immunoaffinity chromatography using an immunoabsorbent column to which an antibody is immobilized which is capable of binding to one or more components of the complex. Such an antibody may be monoclonal or polyclonal in origin. Other useful types of affinity purification for the protein complex may utilize, for example, a solid-phase substrate which binds the catalytic kinase domain of a protein, or an immobilized binding site for noncatalytic domains of the components of the complex, which bind in such a manner as to not disrupt the complex. The complex of the present invention may be biochemically purified from a variety of cell or tissue sources.

Methods for the synthesis of polypeptides or fragments thereof, which are capable of acting as components of the complexes of the present invention, are well-known to those of ordinary skill in the art. See, for example, Creighton, *Proteins: Structures and Molecular Principles*, W.H. Freeman and Co., NY (1983), which is incorporated herein, by reference, in its entirety.

Components of a complex which have been separately synthesized or recombinantly produced, may be reconstituted to form a complex by standard biochemical techniques well known to those skilled in the art. For example, samples containing the components of the complex may be combined in a solution buffered with greater than about 150 mM NaCl, at a physiological pH in the range of 7, at room temperature. For example, a buffer comprising 20 mM. Tris-HCl, pH 7.4, 137 mM NaCl, 10% glycerol, 1% Triton X-100, 0.1% SDS, 0.5% deoxycholate and 2 mM EDTA could be used.

Methods for preparing the components of complexes of the invention by expressing nucleic acid encoding proteins are described herein. Methods which are well known to those skilled in the art can be used to construct expression vectors containing protein coding sequences and appropriate transcriptional and translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989)

A variety of host-expression vector systems may be utilized to express the coding sequences of the components of the complexes of the invention. Such host-expression systems represent vehicles by which the coding sequences of interest may be produced, but also represent cells which may, when transformed or transfected with the appropriate nucleotide coding sequences, exhibit the protein complexes of the invention. These include but are not limited to microorganisms such as bacteria (e.g., *E.coli, B. subtilis*) transformed with recombinant bacteriophage DNA, plasmid DNA or cosmid DNA expression vectors containing protein coding sequences; yeast (e.g., Saccharomyces and Pichia) transformed with recombinant yeast expression vectors containing the protein coding sequences; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the complex being expressed. For example, when large quantities of complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., *EMBO J.* 2:1791, 1983), in which the protein coding sequence may be ligated individually into the vector in frame with the lac Z coding region so that a fusion protein is produced; pIN vectors. (Inouye and Inouye, *Nucleic acids Res.* 13:3101–3109, 1985; Van Heeke & Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned protein can be released from the GST moiety.

In an insect system, *Autographa californica* nuclear polyhidrosis virus (AcNPV) is used as a vector to express foreign genes. The virus grows in Spodoptera frugiperda cells. The complex coding sequence may be cloned individually into non-essential regions (for example the polyhedrin gene) of the virus and placed under control of an AcNPV promoter (for example the polyhedrin promoter). Successful insertion of the PTK/adaptor complex coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., *J. Biol.* 46:584, 1983; Smith, U.S. Pat. No. 4,215,051).

In mammalian host cells, a number of viral based expression systems may be utilized. In cases where an adenovirus is used as an expression vector, the complex coding sequence may be ligated to an adenovirus transcription/translation control complex, e.g. the late promoter and tripartite leader sequence. This chimeric gene may then be inserted in the adenovirus genome by in vitro or in vivo recombination. Insertion into a non-essential region of the viral genome (e.g., region E1 or E3) will result in a recombinant virus that is viable and capable of expressing proteins in infected hosts. (E.g., See Logan & Shenk, *Proc. Natl. Acad. Sci. USA* 81:3655–3659, 1984) Specific initiation signals may also be required for efficient translation of inserted coding sequences. These signals include the ATG initiation codon and adjacent sequences.

In cases where an entire protein gene, including its own initiation codon and adjacent sequences, is inserted into the appropriate expression vector, no additional translational control signals may be needed. However, in cases where only a portion of the coding sequence is inserted, exogenous translational control signals including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987)

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably coexpress both the proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, polyadenylation sites, etc.), and a selectable marker.

Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PTK and adaptor protein. Such engineered cell lines are particularly useful in screening and evaluation of compounds that affect signals mediated by the complexes.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Lowy et al., *Cell* 22:817, 1980) genes can be employed in tk$^-$, hgprt$^-$ or aprt$^-$ cells, respectively. Also, antimetabolite resistance can be used as the basis of selection for dhfr, which confers resistance to methotrexate (Wigler et al., *Natl. Acad. Sci. USA* 77:3567, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al. *Gene* 30:147, 1984) genes.

New members of the protein families capable of forming the complexes of the invention may be identified and isolated by molecular biological techniques well known in the art. For example, a previously unknown protein encoding gene may be isolated by performing a polymerase chain reaction (PCR) using two degenerate oligonucleotide primer pools designed on the basis of highly conserved sequences within domains common to members of the protein family.

The template for the reaction may be cDNA obtained by reverse transcription of mRNA prepared from cell lines or tissue known to express complexes. The PCR product may be subcloned and sequenced to insure that the amplified sequences represent the sequences of a member of the PTK or adaptor subfamily. The PCR fragment may then be used to isolate a full length protein cDNA clone by radioactively labeling the amplified fragment and screening a bacteriophage cDNA library. Alternatively, the labeled fragment may be used to screen a genomic library. For a review of cloning strategies which may be used. See e.g., Maniatis, *Molecular Cloning: A Laboratory Manual*, Cold Springs Harbor Press, N.Y. (1989); and Ausubel et al., *Current Protocols in Molecular Biology*, Green Publishing Associates and Wiley Interscience, N.Y. (1989). A general method for cloning previously unknown proteins has been described by Skolnik (Skolnik, E. Y., *Cell* 65:75, 1991) and Skolnik et al., (U.S. patent application Ser. No. 07/643,237) which are incorporated herein, by reference, in their entirety, including drawings.

XVII. Derivatives of Complexes

Also provided herein are functional derivatives of a complex. By "functional derivative" is meant a "chemical derivative," "fragment," "variant," "chimera," or "hybrid" of the complex, which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" of the complex contains additional chemical moieties not normally a part of the protein. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art. Covalent modifications of the protein complex or peptides are included within the scope of this invention. Such modifications may be introduced into the molecule by reacting, targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate); and bifunctional maleimides such as bis-N-maleimido-1,8-octane. Derivatizing agents such as methyl-3-[p-azidophenyl) dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W.H. Freeman & Co., San Francisco, pp. 79–86 (1983)), acetylation of the Nterminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in *Remington's Pharmaceutical Sciences*, 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein, when present in a complex resembling the naturally occurring complex, are useful for screening for compounds that act to modulate signal transduction, as described below. It is understood that such fragments, when present in a complex may retain one or more characterizing portions of the native complex. Examples of such retained characteristics include: catalytic activity; substrate specificity; interaction with other molecules in the intact cell; regulatory functions; or binding with an antibody specific for the native complex, or an epitope thereof.

Another functional derivative intended to be within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA-coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman-et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

XVIII. Evaluation of Disorders

The protein complexes of the invention involved in disorders may be utilized in developing a prognostic evaluation of the condition of a patient suspected of exhibiting such a disorder. For example, biological samples obtained from patients suspected of exhibiting a disorder involving a protein complex may be assayed for the presence of such complexes. If such a protein complex is normally present, and the development of the disorder is caused by an abnormal quantity of the complex, the assay should compare complex levels in the biological sample to the range expected in normal tissue of the same cell type.

Among the assays which may be undertaken may include, but are not limited to isolation of the protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the protein complex may be present in an abnormal level or in a modified form, relative to the level or form expected is normal, nonnoncogenic tissue of the same cell type. It is possible that overexpression of both components may indicate a particularly aggressive disorder. Thus, an assessment of the individual and levels of mRNA and protein in diseased tissue cells may provide valuable clues as to the course of action to be undertaken in treatment of such a disorder. Assays of this type are well known to those of skill in the art, and may include, but are not limited to, Northern blot analysis, RNAse protection assays, and PCR for determining mRNA levels. Assays determining protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

EXAMPLES

The present invention is described in further detail in the following non-limiting examples.

Example 1

Screening of a Human Skeletal Muscle cDNA Library with Radiolabelled Oligonucleotides Total RNA was isolated from human skeletal muscle by the acid guanidinium thiocyanate-phenol-chloroform extraction procedure as described by Puissant et al., BioTechniques 8:148–149(1990). Poly (A+) RNA was isolated on an oligo(dT) column (Avid et al., Proc. Natl. Acad. Sci. USA 69:1408–1412(1972)). A cDNA library was constructed using the methods described by Okayama and Berg, Mol. Cell. Biol. 2:161–170(1982); Okayama and Berg, Mol. Cell. Biol. 3:280–289(1983). The pCDVI-PL vector was used for preparation of the primer fragment (Noma et al., Nature 319:640–646 (1986)). A short synthetic adapter was used as second strand primer as recently described (Boel, E. et al., BioTechniques 11(1):26–28 (July, 1991)). E. coli DH5α (Gibco BRL, Gaithersburg, Md. 20877, USA) was used for transformation according to the protocols by H. Inuoue et al., Gene 96:23–28 (1990). After transformation, the bacteria were plated on LB plates containing 50 μg/ml ampicillin at a density of about 8000 colonies per 15 cm plate. Nitrocellulose replica filters (Schleicher & Schuell, BA85) were screened with standard colony hybridization technique (Sambrook et al., Molecular Cloning: A Laboratory Manual, Cold Spring Harbor, N.Y. 1989). An equimolar mixture of the following, three oligonucleotides which were labelled at the 5' end using T4 polynucleotide kinase and [γ-$^{32}$P] ATP (Amersham, Braunschweig) (Sambrook et al., 1989) was used for hybridization.

E10 5' AAG GGT TTT ACC ATG GCA GAG AAA 3' SEQ ID NO:3

Met Ala Glu Lys SEQ ID NO:4

E11 5' TTA ACT TGT CGA CTA CGT CAG CAG 3' SEQ ID NO:5

E13 5' A((CT) AT(GT) TGG (GT)CT (AG) GGC TGC ATC 3'SEQ ID NO:6

The nucleotide sequences of the oligonucleotides correspond to nucleotides (nt) 378–401 (E10, including the first in frame methionine-codon) and nt 2033–2010 (E11, reverse primer, including the first in frame stop codon), respectively, of the rat ERK-3 sequence published by Boulton et al., Cell 65:663–675 (1991): with single modifications outside the coding region to introduce new restriction sites (NcoI in E10 and SaII in E11, respectively). E13 was designed as 32 fold degenerate oligonucleotide based on the amino acid sequence of rat ERK1, ERK2 and ERK3 corresponding to nt 1030–1052 of rat erk3 (Boulton et al,. Cell 65:663–675 (1991)).

A total of 10 pmoles of the labelled oligonucleotides E10, E11 and E13 in 50 ml hybridization mixture (6×SSC, 5×Denhardt's solution, 0.05% SDS (Current Protocols in Molecular Biology, M. Ausubei et al., eds., John Wiley & Sons, New York (1988)) were added to replica nitrocellulose filters and allowed to hybridize at 42° C. for 2 h. The filters were washed in 6×SSC, 0.05% SDS three times 10 min first at room temperature, then at 42°, 46°, 48° and 50° C., respectively.

Two positive clones were identified by autoradiography and isolated following the procedure described in Sambrook et al., 1989. Partial dideoxy sequencing (Sanger et al., *Proc. Natl. Acad. Sci. USA* 74:5463–5467(1977) of the two positive clones using oligonucleotide E13 as primer revealed identical nucleotide sequence. The larger clone with an insert of about 1900 bp was then fully sequenced. Sequencing was done using the dideoxynucleotide chain termination method (Sanger et al., *PNAS* 74, 5463–5467 (1977)) with the sequenase kit (version 2.0) (U.S. Biochemicals) according to the manufacturers instruction. The first methionine precedes an open reading frame of 1179 bp encoding a protein of 393 amino acids (FIG. 1, SEQ ID NO:1 and SEQ ID NO:2) or 43.2 kD molecular weight which shows 61% similarity (38% identity) to the human ERK1 peptide sequence, 64% similarity to the rat ERK1 and ERK2 (39% and 37% identity, respectively) and 55% similarity to the rat ERK3 (30% identity) (the comparison program uses the algorithm of Needleman and Wunsch, *J. Mol. Biol.* 48:443–453 (1970)). The new clone was termed human ERK5 (hERk5).

Example 2

Northern Blot Analysis of Human ERK5

Total RNA from normal human tissue was isolated by the acid guanidinium thiocyanate-phenol-chloroform extraction procedure (Puissant and Houdebine, *BioTechniques* 8:148–149 (1990)). The preparation of poly(A+) RNA was performed as described by Aviv and Leder, *Proc. Natl. Acad. Sci. USA* 69:1408–1412(1972). Five $\mu$g of poly(A+) RNA per lane were loaded on a 1.2% agarose-2.2 M formaldehyde gel and after separation blotted onto a nitrocellulose filter using standard techniques (Sambrook et al., 1989).

A $^{32}$P labelled 1200 bp Bam HI fragment of hERK5 in 30 ml of hybridization solution (5×Denhardt's solution, 5×SSC, 5 $\mu$g/ml salmon sperm DNA, 50 mM $Na_2HPO_4$ pH 6.8, 1 mM $NaH_2PO_4/Na_4P_2O_4$, 50% formamide) was used for hybridization over night at 42° C. After washing for 10 min in 2×SSC, 0.1% SDS and for 2×10 min in 0.2×SSC, 0.1% SDS, the filter was exposed for 3 and 14 d, respectively. The $^{32}$P labelling was done using the Random primed DNA labelling Kit (Bat No. 1004760, Boehringer Mannheim Biochemica) according to the manufacturers instruction. Fifty ng of denatured DNA were labelled with 50 $\mu$Ci $^{32}$PDATP with an average incorporation of $2 \times 10^8$–$1 \times 10^9$ cpm/$\mu$g DNA. After the labelling reaction unincorporated $^{32}$PDATP was removed using a Sephadex G50 column. The washed filter was exposed to an X-ray film. Analysis of the Northern Blot showed that there is a major transcript of hERK5 of about 1.9 kb. Further, it appears that hERK5 is preferentially expressed in skeletal muscle.

Example 3

Production of Polyclonal Antibodies Against hERK5

Antibodies were raised against an *E. coli* fusion protein composed of the carboxy-terminal part of glutathione S-transferase and the last 264 amino acids of hERK5 protein. The vector encoding this construct was generated by cloning a 1200 bp BamHI-fragment of hERK5 into the pGEX3X plasmid (Pharmacia, Uppsala) which upstream of the multiple cloning site carries the cDNA for about 250 amino acids (27.5 kD) of glutathione S-transferase under the control of the lac promoter. The construct was transformed in *E. coli* 298F' cells (R. du Bridge, Genentech, San Francisco). After induction with IPTG (1 mM final concentration) the expressed soluble fusion protein was purified on Glutathione-Sepharose 4B (Pharmacia, Uppsala) according to the manufacturer's instruction. The apparent molecular weight in SDS-PAGE is 56 k. The purified fusion protein (100 $\mu$g) was subcutaneously injected into a female rabbit using Freund's adjuvant as described in Harlow and Lane, Antibodies: A Laboratory Manual, Cold Spring Harbor, N.Y. (1988). After the second boost, antiserum was collected and used in Western blotting.

For Western blotting total lysate of *E. coli* clones expressing either the PGEX encoded GST protein portion or the hERK-5-GST fusion protein before and after induction with IPTG was separated on SDS-PAGE. The bacteria were harvested by centrifugation and resuspended in Laemmli sample buffer (4% SDS, 125 mM Tris pH 6.8, 1.0% β-mercapto ethanol, 10% glycerol, 0.02% bromphenol blue) to a concentration of $2 \times 10^7$ cells/$\mu$l of sample buffer. After boiling for 5 min. 10 $\mu$l of this SDS lysate were applied to SDS-PAGE (10% polyacrylanmide), transferred to nitrocellulose using standard techniques (Sambrook et al., (1989), 200 mA, 40 min), blocked with PBS containing 2% nonfat dry milk, 0.02% Tween20, washed (PBS 0.02% Tween 20,0.2% gelatine) and detected with the polyclonal antiserum raised against the hERK-GST fusion protein in comparison to preimmune serum (both sera diluted 1:5000 in PBS containing 0.05% Tween 20 and 0.2% gelatine). The second antibody (horseradish peroxidase coupled goat anti-rabbit IgG (BioRad, Munchen)) was diluted 1:20000 fold in PBS 0.02% Tween 20,0.2% gelatine. Peroxidase reaction was performed using the ECL Kit (Amersham, Braunschweig). The antiserum strongly recognizes a band at 56 kD corresponding to the molecular weight of the hER-GST fusion protein which is not detected by the preimmune serum. There is no cross reactivity of the anti-hEPK5-GST antiserum with the recombinant GST protein portion.

Example 4

Expression of hERK5 in Eukaryotic Cells

The herk 5 cDNA was cloned in the eukaryotic expression vector pcDNAI (Invitrogen, San Diego) and hERK-5 was transiently expressed in human embryonal kidney fibroblasts (293 cells:ATCC CRL 1573). The 293 cells were grown in DMEM with 4.5 mg/ml glucose and 10% FCS. $5 \times 10^4$ cells per 3.5 cm dish were transfected with 10 $\mu$g DNA using the calcium-phosphate precipitation method described by Chen and Okayama, *Mol. Cell. Biol.* 7:2745–2752, 1987. After 16 h at 35° C. and 3% $CO_2$ the medium was changed. The cells were transferred to 37° C. and 5% $CO_2$ for additional 16 h, washed off the cultured dish, collected by centrifugation, and resuspended in Laemmli sample buffer (composition see Example 3, 40 $\mu$l per 3.5 cm dish).

The Western blot of 293 cell SDS-lysate after pcDNAI-herk5 transfection shows major bands at 44 kD (which corresponds to the predicted molecule weight of hERK5) and 46 kD, probably representing a different phosphorylation state of hERK5 protein. There is no cross reactivity with proteins expressed in mock transfected 293 cells.

Example 5

Generation of Stable Cell Lines Expressing hERK5

NIH3T3 cells., immortalized mouse fibroblasts (Jainchill et al., J. Virol. 4:549–553 (1969)) were grown in DMEM with 4.5 mg/ml glucose and 10% FCS to subconfluency and transfected with 20 μg/1×10$^7$ cells of a cvn-construct containing the complete hERK-5 cDNA. The cvn vector carries the Sv40 early promoter, HBV poly A signal as well as a neomycin resistance gene which allows selection of transfected cells on G418 resistance, and the gene for the DHFR which can be used to increase the expression of the integrated cDNA by addition of methotrexate at concentrations of 100–1000 nM to the culture medium (Rosenthal et al., Cell 46:155–169 (1986)). Transfection was performed as described in Example 4. After 16 h at 35° C. and 3% $CO_2$, the medium was changed and the cells were grown at 37° C., 5% $CO_2$ for additional 24 h with one medium change after 8 h. The cells were then split to different dilutions and grown in 1 mg/ml G418 containing medium until cell colonies, appeared which were isolated and selected on methotrexate growth.

The expression of hERK5 was tested in the Western blot of total cell lysate using the antibody raised against the hERK5-GST fusion protein as described in Example 3. The blot shows a double band at 44/46 kD in three of four cell clones tested corresponding to the stably expressed hERK5 protein whose expression is increased when the cells are grown in 200 and 500 mM methotrexate, respectively.

Example 6 cDNA Cloning of herk5

A human cDNA library from skeletal muscle prepared as described by Okayama & Berg (Mol.Cell.Biol. 2:161–170 (1982), Mol.Cell. Biol. 3:280–289 (1983)) was screened with a set of radiolabelled oligonucleotides which, were synthetized on a DNA synthetizer "Cyclone plus" (Milligen). The oligonucleotides had the following sequences: AAG GGT TTT ACC ATG GCA GAG AAA (E10) SEQ ID(NO:3) TTA ACT TGT CGA CTA CGT CAG CAG (E11) SEQ ID(NO:5) and A(CT) AT(GT) TGG (GT) CT G(CT) (AG) GGC TGC ATC (E13) SEQ ID(NO:6) respectively. They correspond to the 5'region (E10, including the first in frame start codon) and the 3'region (E11, including the first in frame stop codon) of rat the ERK3 sequence (Boulton et al., Cell 65:663–675 (1991). Oligonucleotide E13, which is 32 fold degenerate, is designed upon the rat ERK3 sequence within the conserved region in subdomain IX (Hanks et al., Science 241:42–52 (1988)) and includes the codons for the homologous amino acids of rat ERK1 and ERK2.

Oligonucleotides were equimolarilly mixed and labelled with $^{32}$P at the 5'end using T4 polynukleotid kinase (Sambrook et al., Molecular cloning: A laboratory manual, Cold Spring Harbor, N.Y., 1989). Screening was performed as described in Sambrook et al., 1989. Bacteria were plated at a density of 8000 colonies per 15 cm plate. In total 150000 colonies were screened. Nitrocellulose filters (Schleicher & Schuell) were hybridized in 6×SSC, 5×Denhardts solution, 0.05% SDS (Current Protocols in Molecular Biology, M. Ausubel et al., eds. John Wiley & Sons, New York (1988)) containing 10 pmoles of labelled oligonucleotide mixture at 42° C. for 2 h. Filters were washed in 6×SSC, 0.05% SDS for 3×10 min at RT, subsequently at 42, 46, 48 and 50° C., respectively. Isolation of positive colonies was performed as described in Sambrook et al., 1989.

Example 7

Preparation of Antisera

Antisera were generated against two different glutathione-S-transferase fusion proteins with (1) the C-terminal 264 amino acids of hERK5 protein and (2) the complete hERK5 protein (393 amino acids), respectively. Therefore a BamHI fragment encoding the C-terminal part of hERK5 and the complete cDNA of herk5, respectively, were cloned in the pGEX3X vector (Pharmacia). Fusion proteins were expressed in E.coli strain 298F' (Genentech, San Francisco), purified as described by Smith & Johnson (Gene 67:31–40, (1988)) and used for immunization of rabbits.

After the second boost, animals were bled and antisera were tested in Western Blot and immunoprecipitation. Antiserum 19 which was raised against the fusion protein containing the C-terminal portion of the hERK5 protein recognized the denaturated protein in the Western Blot (dilution 1:5000), but failed in the immunoprecipitation. The antiserum raised against the complete hERK5 fusion protein (As 23) was able to specifically precipitate native hERK5 protein (dilution 1:300) in lysate of transfected cells, but did not react in the Western Blot.

Example 8

Mutagenesis

In order to introduce an amino acid exchange of one of the two regulatory phosphorylation sites of MAP Kinases in the hERK5 cDNA, codon 185 (TAC, encoding Y) was changed on the second postition to TTC (encoding F) by using PCR with specific oligonucleotides carrying one mismatch at the indicated position.

Example 9

Overexpression of hERK5 Protein in 293 Cells

For transient expression in human embryonal kidney fibroblasts (293 cells) (Graham et al., J. Gen. Virology 36:59–77 (1977)) the hERK5 wt and Y185F mutant cDNAs, respectively, were cloned in a cytomegaloviral promoter driven expression vector (Gorman et al., Virology 171:377–385 (1989)). Cells were grown in DMEM supplemented with 10 FCS (Gibco) at 5% $CO_2$ and 37° C. Transfection was carried out according to the method described by Chen & Okayama (Mol. Cell. Biol. 7:2745–2752 (1987)). Cells were seeded at a density of 2×10$^5$ per 3.5 cm dish 8 h before transfection. Cesium chloride purified supercoiled DNA (in total 10 μg per 3.5 cm dish) was mixed with 0.25 M $CaCl_2$ in a total volume of 100 μl. After dropwise addition of 100 μl 2×BBS (50 mM BES pH 6.96, 280 mM NaCl, 1.5 mM $NaHPO_4$) under vortexing, the solution was incubated for 15 min at RT. Medium of cells was changed during this time. (2 ml per 3.5 cm dish) and the DNA mixture was added. Cells were then incubated for 16 h at 3% $CO_2$ and 35° C. After this time the medium was removed and replaced by either DMEM supplemented with 0.5% FCS to starve cells-for 24 h before stimulation with insulin, or by DMEM supplemented with 10% FCS. Cells were then grown at 5% $CO_2$ and 37° C.

Insulin stimulation was performed when cells had been cotransfected with the cDNA for the human insulin receptor A-type, cloned in the expression vector mentioned above, with a final insulin concentration of 10$^{-8}$M for 10 min. For metabolic labelling, growth medium was replaced by methionine free MEM (Gibco) containing 60 μCi $^{35}$S methionine (Amersham) per ml and dialyzed FCS at a concentration of 0.5% and 10%, respectively, 16 h prior to lysis.

For cell lysis dishes were placed on ice, growth medium was removed and lysis buffer (20 mM HEPES NaOH pH 7.5, 150 mM NaCl, 10% glycerol, 1% Triton X100, 1.5 mM $MgCl_2$, 1 mM EGTA, 1 mM PMSF, 1 mM orthovanadate, 50 mM NaF) was added. After 15 min, cells were scraped off, resuspended carefully, incubated another 5 min on ice and centrifuged for 5 min at 4° C. in an Eppendorf centrifuge. The lysate was diluted 1:6 in HNTG (20 mM HEPES NaOH pH 7.5, 150 mM NaCl, 10% glycerol, 0.1% Triton X100, 1 mM PMSF, 1 mM orthovanadate, 50 mM NaF). Protein-A-Sepharose and anti-hERK5-antiserum were added.

After incubation for 3.5 h at 4° C. on a rotating wheel, the immuncomplex was washed 3× in HNTG and resuspended in three volumes of SDS-sample buffer (62.5 mM Tris-HCl 7.0, 3% SDS, 10% glycerol, 10% β-mercaptoethanol, 0.05% bromphenol blue). After boiling for 5 min, samples were electrophorized on a 10% SDS-polyacrylamid gel. The gel was fixed in 10% acetic acid, 40% methanol, treated with 1 M sodium-salicylate, 30% methanol to increase the signal, dried and exposed to a Kodak XAR film at −70° C.

Example 10

Kinase Assay in MBP Containing Polyacrylamid Gels

Unlabelled anti-hERK5-immunoprecipitates of transfected 293 cells were electrophorized on a 10% SDS-polyacrylamid gel (0.5 mm thick and 6 cm long) containing 0.5 mg/ml MBP from bovine brain (Sigma). The assay was performed according to the procedure described in Lee et al., J.Biol.Chem. 266:5255–5263 (1993).

After electrophoresis, proteins were fixed in 20% isopropanol, 50 mM Tris-HCl pH 8.0 (2 changes à 100 ml) for 1 h at RT. SDS was removed by washing the gel with 250 ml of 50 mM Tris-HCl pH 8.0, 5 mM β-mercaptoethanol for 1 h at RT. After denaturation in 6 M guanidinium HCl for 1 h at RT (2 changes à 100 ml), proteins were renatured by washing with 50 mM Tris-HCl pH 8.0, 0.04% Tween 40, 5 mM β-mercaptoethanol for 16 h at 4° C. (5 changes à 250 ml). The gel was then preincubated in 10 ml of 40 mM HEPES NaOH pH 8.0, 2 mM DTT, 10 mM $MgCl_2$ for 1 h at RT. Phorphorylation of MBP was carried out in 10 ml of 40 mM HEPES NaOH pH 8.0, 50 µCi gamma$^{32}$P ATP, 40 µM ATP, 10 MM $MgCl_2$, 0.5 mM EGTA for 1 h at RT. After extensive washing in 5% (w/v) TCA, 1% sodium-pyrophosphate, the gel was dried and exposed to a Kbdak XAR film at −70° C. with intensifying screen.

Example 11

Stable Overexpression of hERK5 wt and Y185F Mutant in NIH3T3 and C2C12 Cells

In order to obtain stably hERK5 overexpressing C2C12 cells, retroviruses were generated which contain the cDNA for hERK5 wt and Y185F mutant, respectively. The hERK5 cDNAs were cloned into the Moloney murine leukemia virus-based retroviral vector pLXSN (Miller & Rosman, Biotechniques 7: 980–990, 1989). The hERK5 cDNA of this plasmid is transcribed from the retroviral long terminal repeat, and the neomycin phosphotransferase gene, conferring resistance to the antibiotic G418, is transcribed from an internal SV 40 promoter. The pLXSN which expresses only the neomycin phosphotransferase gene, was used as control vector.

Amphotropic retroviruses were generated in the packaging cell line PA317 (Miller & Buttimore,. Mol.Cell.Biol. 6:2895–2902, 1986). The cells were transfected with the pLXSN constructs as described in 5 and grown in DMEM containing 4.5 mg/ml glucose and 10% FCS for 48 h before culture supernatant was collected.

To obtain ecotropic retroviruses of higher titer, the packaging cell line GP+E86 (Markowitz et al., J.Virol. 62: 1120–124, 1988) was infected with supernatant of PA317 cells containing 10 mg/ml polybren for 12 h. Cells were then selected on G418 resistance in DMEM 4.5 mg/ml glucose and cloned. Supernatant of hERK5 expressing single cell clones was collected and used to infect C2C12 cells (Yaffe & Saxel, Nature 270, 725–727, 1977) as described for GP+E86 cells. Selected G418 resistant polyclonal cell lines were tested for expression of the hERK5 proteins by Western Blotting of total SDS-lysates and immunodetection with antiserum 19 (see Material and Methods). Therefore proteins were separated on a 10% SDS-polyacrylamid gel, blotted onto nitrocellulose (Schleicher & Schuell) (Towbin et al., PNAS 76:4350–4354 (1979)) and incubated in diluted AS 19 at 4° C. over night. Detected protein bands were visualized using horseradish-peroxidase coupled goat-anti-rabbit-IgG-antibodies (BioRad) and the ECL kit (Amersham).

Example 12

Stimulation of hERK5 wt and Y185F in Infected NIH3T3 and

C2C12 Cells

In order to investigate the ability of different signals to activate hERK5 and endogenous MAP Kinases ERK1 and ERK2, overexpressing retroviral infected NIH3T3 and C2C12 cells, respectively, were grown in medium containing 10% FCS until subconfluency, then starved for 24 h in 0.5% FCS and treated either with 2 mM Na-orthovanadate (2 h). without or together with 10% FCS (last 10 min), 1 mM TPA (10 min) without or together with 2 mM Na-orthovanadate (10 min prior to addition of TPA), 1 nM ocadaic acid (2 h) alone or together with either 1 mM TPA (last 10 min) or 10% FCS (last 10 min), or treated with $10^{-7}$M and $10^{-8}$M insulin, respectively, or left untreated. For lysis, cells were put on ice, washed once with cold PBS and resuspended in Laemmli-buffer.

About 60 µg protein per lane were applied to 10% SDS-PAGE and blotted onto nitrocellulose (Schleicher & Schuell, BA 85) (Towbin et al., PNAS 76: 4350–4354 (1979)). Immunodetection of hERK5 was. performed with antiserum 19; endogenous ERK1 and ERK2 of NIH3T3 and C2C12 cells were visualized using a specific polyclonal rabbit antiserum (Santa Cruz Biotechnologies) which recognizes both MAP KInase isoforms. Decorated proteins were visualized using horseradish-peroxidase coupled goat-anti-rabbit-IgG-antibodies (Biorad) and the ECL kit (Amersham).

Example 13

Fusion Experiments in Infected C2C12 Myoblasts

In order to investigate the role of hERK5 during differentiation-of C2C12 myoblasts, infected cells were seeded in proliferation medium at a density of 125000 cells per 3.5 cm plate (12000 cells per cm$^2$) and grown for 48 h. Confluent cells were then washed once with serum free medium and induced to fuse under low serum conditions, i.e. medium containing 2% horse serum. 3, 5 and 7 d after medium: change, the state of fusion was documented.

Example 14 cDNA Cloning of hERK5

A human skeletal muscle cDNA library was screened with a set of oligonucleotides corresponding to sequences of rat ERK3 as described above. Two positive clones of different length were isolated whose nucleotide sequences turned out. to be identical. The first in frame start codon of the larger clone precedes an open reading frame of 1179 bp encoding a 393 amino acids protein with a predicted of molecular weight of 43.2 kD. The nucleotide sequence preceding the inititation codon corresponds well to the consensus sequence described by Kozak, *Nucl. Acids Research* 15: 8125–8148, 1987.

Sequence comparison using the program of Needleman and Wunsch, *J.Mol.Biol.* 48:443–453, 1970 revealed 63% similarity (39% identity) of the new sequence with hERK1, 65% similarity (38% identity) with hERK2 and 61% similarity (33% identity) with hERK3, respectively (human ERK sequences were taken from Gonzalez et al., *FEBS letters* 304: 170–178, 1992). Detailed sequence analysis according to the criteria of. Hanks et al., *Science* 241:42–52, 1988 as well as conservation of the three residues which are essential for activity in ERKs (lysine residue in subdomain II at amino acid positon 57 in Xenopus MAPK (Posada & Cooper, *Science* 255:212–215, 1992) or position 52 in mouse ERK2 (Her et al., *Nucl.Acid Res.* 19:3743, 1991) as well as T183 and Y185 (Payne et al., *EMBO J.* 10:885–892, 1991) in subdomain VIII indicate that the new sequence encodes an additional member of the extracellular signal regulated serine threonine kinase family. The sequence was therefore termed hERK5.

Example 15

Expression of hERK5 in Normal Human Tissue

To investigate the tissue distribution of hERK5, we used poly $A^+$ RNA of normal human tissue for a Northern Blot which was probed with a radiolabelled fragment of hERK5 cDNA encoding the C-terminal 263 amino acids followed by the 3'untranslated region. After 3 d of exposure, the autoradiograph of the blot demonstrated hybridization of the probe with a single mRNA species of approximately 1.9 kb which corresponds to the size of the cloned cDNA. A further exposure for 14 d indicates that among the tissues tested, the expression of hERK5 seems to be restricted to skeletal muscle.

Example 16

Overexpression of hERK5 in 293 Cells

For overexpression of hERK5 protein in a human cell system, 293 cells were transfected as described above with an expression vector containing hERK5 wt or Y185F mutant cDNA. Expression vector cDNA was used as control vector. Mutation of tyrosine residue 185 to phenylalanine was performed as described above to gain a form of hERK5 which lacks one of the two regulatory phosphorylation sites and thus should be impaired in kinase activity. Cells were grown in 10% FCS and metabolically labelled with $^{35}$S-methionine. The Triton X100 lysate was incubated with antiserum 23 and protein-A-sepharose. After SDS-PAGE, the precipitate was visualized by autoradiography of the dried gel. The hERK5 protein is a double band of 44/46 kD as well as a comparably weaker band of 56 kD size in transfected cells. There is no endogeneous hERK5 protein detectable under these conditions in untransfected 293 cells.

To investigate whether any of these bands represents a particular phosphorylation status of hERK5 protein in response to an extracellular signal like insulin which has been shown to activate MAP kinases (Ray & Sturgill, *J.Biol.Chem.* 263:12721–12727, 1988), Rossomando et al., *PNAS* 86:6949–6943, 1989, Boulton et al., *Cell* 65:663–675, 1991), 293 cells were transiently cotransfected with either the hERK5 wt cDNA or the Y185F mutant cDNA together with the human insulin receptor A-type cDNA, all cloned under the cytomegaloviral promoter of the expression vector mentioned above. The transfected cells were starved in medium supplemented with 0.5% FCS 24 h prior to stimulation with insulin, metabolically labelled with $^{35}$S-methionine, lysed and treated as described above. Major bands of 44/46 kD can be observed as well as a band of 56 kD which might represent some kind of modified hERK5 protein since it is recognized by antiserum 19 in the Western Blot of total lysate of transfected 293 cells as well. However, in infected NIH3T3 or C2C12 cells which overexpress hERK5 more moderately than transfected 293 cells, this band is clearly much weaker than the 44/46 kD doublet, both in immunoprecipitation and Western blot, indicating that its appearance correlates with the level of hERK5 overexpression.

The shift from 44 to 46 kD is caused by phosphorylation events as could be demonstrated by treating transfected 293 cells with orthovanadate and Western blotting of total SDS-lysates with anti-phosphotyrosine as well as anti-hERK5-antiserum where both, the species of 46 kD as well as the 56 kD band appear to be tyrosine-phosphorylated in hERK5 wt, but not in the Y185F mutant.

However, neither in the 293 overexpression system nor in infected NIH3T3 cells, the 4.4/46 kD shift could be induced by treating starved cells with FCS or ligands of coexpressed insulin or epidermal growth factor receptor, respectively, whereas endogeneous ERK1 and ERK2 shifted under these conditions. This result indicates that hERK5 does not seem to be activated via the same signal transduction pathways as are endogeneous ERK1 and ERK2.

Example 17

MBP Kinase Assay of hERK5

To investigate the MBP kinase activity of hERK5, the cDNAs of hERK5 wt as well as the Y185F mutant were expressed in 293 cells together with the. insulin receptor A-type cDNA as described above. The 293 cell system was used in order to provide high amounts of protein which should allow to detect even low protein kinase activity. Cells were starved and stimulated or not with insulin for 10 min. HERK5 protein was immunoprecipitated with antiserum 23 and applied to SDS-PAGE in a gel containing MBP as substrate. The assay was performed as described above.

A predominant signal is observed at 56 kD corresponding to the band which is detected by the antisera both in Western Blot and immunoprecipitation of hERK5 protein in 293 cells. A weaker signal at the position of the 44/46 kD bands indicates either autophosphorylation of hERK5 as described for recombinant ERK1 and ERK2 in vitro (Crews et al., *PNAS* 88:8845–8849, 1991, Seger et al., *PNAS* 88:6142–6146, Wu et al., *PNAS* 88:9508–9512, 1991) or lower MPB kinase activity due to partial activation. There is no significant difference in MBP kinase activity between stimulated or non stimulated cells which is consistent with the results described before. As the lack of $^{32}$P incorporation in lanes 5 and 6 demonstrates, the tyrosine residue in amino acid position 185 in hERK5 seems to play an essential role for its enzymatic activity. Mutation of this residue which is conserved among all active MAP kinases might abolish activating phosphorylation and thus renders the hERK5 molecule kinase inactive.

Example 18

Overxpression and Activation of hERK5 in NIH3T3 and C2C12 Cells

Phosphorylation events on hERK5 protein were investigated in stably expressing retrovirally infected NIH3T3 and C2C12 cells as a more moderate overexpression system. NIH3T3 and C2C12 cells, respectively, were infected as described above, selected on G418 resistance and tested for expression. Subconfluent cells were starved for 24 h in 0.5% FCS and then treated with orthovanadate, TPA, ocadaic acid, insulin and FCS, respecitively, as described above. Immunodetection of blotted total lysates after SDS-PAGE with antiserum 19 revealed basically the same picture for infected NIH3T3 and C2C12 cells.

Whereas endogeneously expressed ERK1 and ERK2, detected by a specific antiserum (Santa Cruz Biotechnology), shift upon insulin, TPA, orthovanadate and FCS treatment, respectively, the electrophoretic mobility of overexpressed hERK5 is reduced only after orthovanadate treatment and does not change when cells are stimulated with insulin or FCS. Futhermore, neither the overexpression of hERK5 wt nor the Y185F mutant alters the activation of endogeneously expressed ERK1 and ERK2. This result suggests that hERK5 and ERK1/2 do not share the same activating signalling cascade or stimulating agents in NIH3T3 and C2C12 cells. However, it also shows that hERK5 can be activated either by autophosphorylation or by a MAP Kinase kinase when phosphotyrosine phosphatases are blocked by orthovanadate.

Example 19

Influence of hERK5 on Fusion of C2C12 Myoblasts

Since Northern Blot analysis of hERK5 revealed strong expression in skeletal muscle, we were interested in whether hERK5 could influence differentiation of myogenic cells like the mouse myoblast cell line C2C12 which can be induced to form multinucleated myotubes upon serum withdrawal under high cell density conditions.

In order to obtain an answer to this question, C2C12 cells were retrovirally, infected to stably express hERK5 wt and the kinase negative Y185F mutant of hERK5, respectively. Infected cells were grown to confluency and then switched to low serum conditions as described above, to induce myoblast fusion.

The development of multinucleated myotubes up to 7 d after change to low serum conditions was observed. C2C12 cells expressing the wt form of hERK5 (Pictures 2, 5 and 8) show a more rapid kinetic of fusion leading to a significantly elevated number of myotubes compared to mock infected C2C12 cells (pLXSN, pictures 1, 4, and 7) after 7 d. The lack of fused cells as well as the appearance of multilayers. in cells expressing the kinase negative form of hERK5 (hERK5-Y185F, pictures 3, 6 and 9) demonstrates that hERK5-Y185F mutant reduces myotube formation by inhibiting withdrawal from the cell cycle prior to fusion and thus retaining the cells in a proliferative state.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An antibody having a specific binding affinity to a polypeptide consisting of at least 9 contiguous amino acids of SEQ ID. NO. 2.

2. The antibody of claim 1, wherein said antibody is a monoclonal antibody.

3. A kit comprising:
   i) a first container means containing the antibody according to claim 1, and
   ii) a second container means containing a reagent capable of detecting the presence of a bound antibody.

4. A hybridoma which produces the monoclonal antibody according to claim 1.

5. The antibody according to claim 1, wherein the polypeptide consists of at least 20 contiguous amino acids of SEQ ID. NO. 2.

6. The antibody according to claim 1, wherein the polypeptide consists of at least 25 contiguous amino acids of SEQ ID. NO. 2.

7. An antibody having a specific binding affinity to a polypeptide consisting of SEQ ID. NO. 2.

8. A kit comprising:
   i) a first container means containing the antibody according to claim 7, and
   ii) a second container means containing a reagent capable of detecting the presence of a bound antibody.

9. An antibody having a specific binding affinity to a polypeptide consisting of at least 264 contiguous amino acids of SEQ ID. NO. 2.

10. A kit comprising:
    i) a first container means containing the antibody according to claim 9, and
    ii) a second container means containing a reagent capable of detecting the presence of a bound antibody.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 1260 base pairs
        (B) TYPE: nucleic acid
        (C) STRANDEDNESS: single
        (D) TOPOLOGY: linear (ix) FEATURE:
        (A) NAME/KEY:    CDS
        (B) LOCATION:    34..1215

(xi) SEQUENCE DESCRIPTION: SEQ ID NO: 1:

```
GGCTCTGCGG GGTGGGCAGC TCCCGGGCCT GCC ATG AGC TCT CCG CCG CCC GGN        54
                                  Met Ser Ser Pro Pro Pro Gly
                                    1               5

GGC AGT GGC TTT TAC CGC CAG GAG GTG ACC AAG ACG GCC TGG GAG GTG        102
Gly Ser Gly Phe Tyr Arg Gln Glu Val Thr Lys Thr Ala Trp Glu Val
```

-continued

```
                      10                      15                      20
CGC GCC GTG TAC CGG GAC CTG CAG CCC GTG GGC TCG GGC GCC TAC GGC        150
Arg Ala Val Tyr Arg Asp Leu Gln Pro Val Gly Ser Gly Ala Tyr Gly
    25                      30                      35

GCG GTG TGC TCG GCC GTG GAC GGC CGC ACC GGC GCT AAG GTT GCC ATC        198
Ala Val Cys Ser Ala Val Asp Gly Arg Thr Gly Ala Lys Val Ala Ile
40                      45                      50

AAG AAG CTG TAT CGG CCC TTC CAG TCC GAG CTG TTC GCC AAG CTC GCC        246
Lys Lys Leu Tyr Arg Pro Phe Gln Ser Glu Leu Phe Ala Lys Leu Ala
                60                      65                      70

TAC CGC GAG CTG CGC CTG CTC AAG CAC ATG CGC CAC GAG AAC GTG ATC        294
Tyr Arg Glu Leu Arg Leu Leu Lys His Met Arg His Glu Asn Val Ile
        75                      80                      85

GGG CTG CTG GAC GTA TTC ACT CCT GAT GAG ACC CTG GAT GAC TTC ACG        342
Gly Leu Leu Asp Val Phe Thr Pro Asp Glu Thr Leu Asp Asp Phe Thr
            90                      95                     100

GAC TTT TAC CTG GTG ATG CCG TTC ATG GGC ACC GAC CTG GGC AAG CTC        390
Asp Phe Tyr Leu Val Met Pro Phe Met Gly Thr Asp Leu Gly Lys Leu
    105                     110                     115

ATG AAA CAT GAG AAG CTA GGC GAG GAC CGG ATC CAG TTC CTC GTG TAC        438
Met Lys His Glu Lys Leu Gly Glu Asp Arg Ile Gln Phe Leu Val Tyr
120                     125                     130                 135

CAG ATG ATG AAG GGG CTG AGG TAT ATC CAC GCT GCC GGC ATC ATC CAC        486
Gln Met Met Lys Gly Leu Arg Tyr Ile His Ala Ala Gly Ile Ile His
                140                     145                     150

AGA GAC CTG AAG CCC GGC AAC CTG GCT GTG AAC GAA GAC TGT GAG CTG        534
Arg Asp leu Lys Pro Gly Asn Leu Ala Val Asn Glu Asp Cys Glu Leu
        155                     160                     165

AAG ATC CTG GAC TTC GGC CTG GCC AGG CAG GCA GAC AGT GAG ATG ACT        582
Lys Ile Leu Asp Phe Gly Leu Ala Arg Gln Ala Asp Ser Glu Met Thr
            170                     175                     180

GGG TAC GTG GTG ACC CGG TGG TAC CGG GCT CCC GAG GTC ATC TTG AAT        630
Gly Tyr Val Val Thr Arg Trp Tyr Arg Ala Pro Glu Val Ile Leu Asn
    185                     190                     195

TGG ATC GCG TAC ACG CAG ACG GTG GAC ATC TGG TCT GTG GGC TGC ATC        678
Trp Ile Ala Tyr Thr Gln Thr Val Asp Ile Trp Ser Val Gly Cys Ile
200                     205                     210                 215

ATG GCG GAG ATG ATC ACA GGC AAG ACG CTG TTC AAG GGC AGC GAC CAC        726
Met Ala Glu Met Ile Thr Gly Lys Thr Leu Phe Lys Gly Ser Asp His
                220                     225                     230

CTG GAC CAG CTG AAG GAG ATC ATG AAG GTG ACG GGG ACG CCT CCG GCT        774
Leu Asp Gln Leu Lys Glu Ile Met Lys Val Thr Gly Thr Pro Pro Ala
        235                     240                     245

GAG TTT GTG CAG CGG CTG CAG AGC GAT GAG GCC AAG AAC TAC ATG AAG        822
Glu Phe Val Gln Arg Leu Gln Ser Asp Glu Ala Lys Asn Tyr Met Lys
            250                     255                     260

GGC CTC CCC GAA TTG GAG AAG AAG GAT TTT GCC TCT ATC CTG ACC AAT        870
Gly Leu Pro Glu Leu Glu Lys Lys Asp Phe Ala Ser Ile Leu Thr Asn
    265                     270                     275

GCA AGC CCT CTG GCT GTG AAC CTC CTG GAG AAG ATG CTG GTG CTG GAC        918
Ala Ser Pro Leu Ala Val Asn Leu Leu Glu Lys Met Leu Val Leu Asp
280                     285                     290                 295

GCG GAC ATC AGG TTG ACT GCA GGC GAG TTT CTT TCC CAT CCC TAC TTC        966
Ala Asp Ile Arg Leu Thr Ala Gly Glu Phe Leu Ser His Pro Tyr Phe
                300                     305                     310

GAG TCC CTG CAC GAC ACG GAA GAT GAG CCC CAG GTC CAG AAG TAT GAT       1014
Glu Ser Leu His Asp Thr Glu Asp Glu Pro Gln Val Gln Lys Tyr Asp
        315                     320                     325

GAC TCC TTT GAC TAC TTT GAC CGC ACA CTG GAT GAA TGG AAG CCG TGT       1062
```

```
Asp Ser Phe Asp Tyr Phe Asp Arg Thr Leu Asp Glu Trp Lys Pro Cys
            330                 335                 340

TAC TTA CAA AGA GGT GCT CAG CTT CAA GCC TCC CCG GCA GCT GGG GGC         1110
Tyr Leu Gln Arg Gly Ala Gln Leu Gln Ala Ser Pro Ala Ala Gly Gly
        345                 350                 355

CAG GGT CTC CAA GGA GAC GCC TCT GTG AAG ATC TCT GGG CTC CGG GGT         1158
Gln Gly Leu Gln Gly Asp Ala Ser Val Lys Ile Ser Gly Leu Arg Gly
360                 365                 370                 375

GGC AGT GAG GAC CAC CTT CAC CTT CCA CCT GAG AGG GGA CTC TCG TTG         1206
Gly Ser Glu Asp His Leu His Leu Pro Pro Glu Arg Gly Leu Ser Leu
                380                 385                 390

CCA CCT TGACCTTGGC TGGGGCTTGC ATCCCAAGGC ATCCATCAGA GCAGACGC            1260
Pro Pro (2) INFORMATION FOR SEQ ID NO: 2 :

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO: 2:

Met Ser Ser Pro Pro Gly Gly Ser Gly Phe Tyr Arg Gln Glu Val
 1               5                  10                  15

Thr Lys Thr Ala Trp Glu Val Arg Ala Val Tyr Arg Asp Leu Gln Pro
            20                  25                  30

Val Gly Ser Gly Ala Tyr Gly Ala Val Cys Ser Ala Val Asp Gly Arg
        35                  40                  45

Thr Gly Ala Lys Val Ala Ile Lys Lys Leu Tyr Arg Pro Phe Gly Ser
50                  55                  60

Glu Leu Phe Ala Lys Leu Ala Tyr Arg Glu Leu Arg Leu Leu Lys His
65                  70                  75                  80

Met Arg His Glu Asn Val Ile Gly Leu Leu Asp Val Phe Thr Pro Asp
                85                  90                  95

Glu Thr Leu Asp Asp Phe Thr Asp Phe Tyr Leu Val Met Pro Phe Met
            100                 105                 110

Gly Thr Asp Leu Gly Lys Leu Met Lys His Glu Lys Leu Gly Glu Asp
        115                 120                 125

Arg Ile Gln Phe Leu Val Tyr Gln Met Met Lys Gly Leu Arg Tyr Ile
130                 135                 140

His Ala Ala Gly Ile Ile His Arg Asp Leu Lys Pro Gly Asn Leu Ala
145                 150                 155                 160

Val Asn Glu Asp Cys Glu Leu Lys Ile Leu Asp Phe Gly Leu Ala Arg
                165                 170                 175

Gln Ala Asp Ser Glu Met Thr Gly Tyr Val Val Thr Arg Trp Tyr Arg
            180                 185                 190

Ala Pro Glu Val Ile Leu Asn Trp Ile Ala Tyr Thr Gln Thr Val Asp
        195                 200                 205

Ile Trp Ser Val Gly Cys Ile Met Ala Glu Met Ile Thr Gly Lys Thr
210                 215                 220

Leu Phe Lys Gly Ser Asp His Leu Asp Gln Leu Lys Glu Ile Met Lys
225                 230                 235                 240

Val Thr Gly Thr Pro Pro Ala Glu Phe Val Gln Arg Leu Gln Ser Asp
                245                 250                 255

Glu Ala Lys Asn Tyr Met Lys Gly Leu Pro Glu Leu Glu Lys Lys Asp
```

```
                    260                 265                 270
Phe Ala Ser Ile Leu Thr Asn Ala Ser Pro Leu Ala Val Asn Leu Leu
            275                 280                 285
Glu Lys Met Leu Val Leu Asp Ala Asp Ile Arg Leu Thr Ala Gly Glu
            290                 295                 300
Phe Leu Ser His Pro Tyr Phe Glu Ser Leu His Asp Thr Glu Asp Glu
305                 310                 315                 320
Pro Gln Val Gln Lys Tyr Asp Asp Ser Phe Asp Tyr Phe Asp Arg Thr
                    325                 330                 335
Leu Asp Glu Trp Lys Pro Cys Tyr Leu Gln Arg Gly Ala Gln Leu Gln
            340                 345                 350
Ala Ser Pro Ala Ala Gly Gly Gln Gly Leu Gln Gly Asp Ala Ser Val
            355                 360                 365
Lys Ile Ser Gly Leu Arg Gly Gly Ser Glu Asp His Leu His Leu Pro
            370                 375                 380
Pro Glu Arg Gly Leu Ser Leu Pro Pro
385                 390
```

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 3:

AAGGGTTTTA CCATGGCAGA GAAA                                   24

(2) INFORMATION FOR SEQ ID NO: 4:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO: 4:

Met Ala Glu Lys
1

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 5:

TTAACTTGTC GACTACGTCA GCAG                                   24

(2) INFORMATION FOR SEQ ID NO: 6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 6:

ACTATGTTGG GTCTGCTAGG GCTGCATC                               28

(2) INFORMATION FOR SEQ ID NO: 7:

(i) SEQUENCE CHARACTERISTICS:
        (A) LENGTH: 404 amino acids
        (B) TYPE: amino acid
        (D) TOPOLOGY: linear (ii) MOLECULE TYPE: protein (xi) SEQUENCE DESCRIPTION: SEQ ID NO: 7:

```
Gly Ser Ala Gly Trp Ala Ala Pro Gly Pro Ala Met Ser Ser Pro Pro
 1               5                  10                  15

Pro Thr Arg Ser Gly Phe Tyr Arg Gln Glu Val Thr Lys Thr Ala Trp
            20                  25                  30

Glu Val Arg Ala Val Tyr Arg Asp Leu Gln Pro Val Gly Ser Gly Ala
        35                  40                  45

Tyr Gly Ala Val Cys Ser Ala Val Asp Gly Arg Thr Gly Ala Lys Val
50                  55                  60

Ala Ile Lys Lys Leu Tyr Arg Pro Phe Gln Ser Glu Leu Phe Ala Lys
65                  70                  75                  80

Leu Ala Tyr Arg Glu Leu Arg Leu Leu Lys His Met Arg His Glu Asn
                85                  90                  95

Val Ile Gly Leu Leu Asp Val Phe Thr Pro Asp Glu Thr Leu Asp Asp
            100                 105                 110

Phe Thr Asp Phe Tyr Leu Val Met Pro Phe Met Gly Thr Asp Leu Gly
        115                 120                 125

Lys Leu Met Lys His Glu Lys Leu Gly Glu Asp Arg Ile Gln Phe Leu
130                 135                 140

Val Tyr Gln Met Met Lys Gly Leu Arg Tyr Ile His Ala Ala Gly Ile
145                 150                 155                 160

Ile His Arg Asp Leu Lys Pro Gly Asn Leu Ala Val Asn Glu Asp Cys
                165                 170                 175

Glu Leu Lys Ile Leu Asp Phe Gly Leu Ala Arg Gln Ala Asp Ser Glu
            180                 185                 190

Met Thr Gly Tyr Val Val Thr Arg Trp Tyr Arg Ala Pro Glu Val Ile
        195                 200                 205

Leu Asn Trp Ile Ala Tyr Thr Gln Thr Val Asp Ile Trp Ser Val Gly
210                 215                 220

Cys Ile Met Ala Glu Met Ile Thr Gly Lys Thr Leu Phe Lys Gly Ser
225                 230                 235                 240

Asp His Leu Asp Gln Leu Lys Glu Ile Met Lys Val Thr Gly Thr Pro
                245                 250                 255

Pro Ala Glu Phe Val Gln Arg Leu Gln Ser Asp Glu Ala Lys Asn Tyr
            260                 265                 270

Met Lys Gly Leu Pro Glu Leu Glu Lys Lys Asp Phe Ala Ser Ile Leu
        275                 280                 285

Thr Asn Ala Ser Pro Leu Ala Val Asn Leu Leu Glu Lys Met Leu Val
290                 295                 300

Leu Asp Ala Asp Ile Arg Leu Thr Ala Gly Glu Phe Leu Ser His Pro
305                 310                 315                 320

Tyr Phe Glu Ser Leu His Asp Thr Glu Asp Glu Pro Gln Val Gln Lys
                325                 330                 335

Tyr Asp Asp Ser Phe Asp Tyr Phe Asp Arg Thr Leu Asp Glu Trp Lys
            340                 345                 350

Pro Cys Tyr Leu Gln Arg Gly Ala Gln Leu Gln Ala Ser Pro Ala Ala
        355                 360                 365
```

```
Gly Gly Gln Gly Leu Gln Gly Asp Ala Ser Val Lys Ile Ser Gly Leu
    370                 375                 380
Arg Gly Gly Ser Glu Asp His Leu His Leu Pro Pro Glu Arg Gly Leu
385                 390                 395                 400
Ser Leu Pro Pro
```

(2) INFORMATION FOR SEQ ID NO: 8 :

(i) SEQUENCE CHARACTERISTICS:
        (A) LENGTH: 355 amino acids
        (B) TYPE: amino acid
        (D) TOPOLOGY: linear (ii) MOLECULE TYPE: protein (xi) SEQUENCE DESCRIPTION: SEQ ID NO: 8:

```
Pro Gly Glu Val Glu Met Val Lys Gly Gln Pro Phe Asp Val Gly Pro
  1                 5                  10                 15
Arg Tyr Thr Gln Leu Gln Tyr Ile Gly Glu Gly Ala Tyr Gly Met Val
             20                  25                 30
Ser Ser Ala Tyr Asp His Val Arg Lys Thr Arg Val Ala Ile Lys Lys
         35                  40                  45
Ile Ser Pro Phe Glu His Gln Thr Tyr Cys Gln Arg Thr Leu Arg Glu
 50                  55                  60
Ile Gln Ile Leu Leu Arg Phe Arg His Glu Asn Val Ile Gly Ile Arg
 65                  70                  75                 80
Asp Ile Leu Arg Ala Ser Thr Leu Glu Ala Met Arg Asp Val Tyr Ile
             85                  90                  95
Val Gln Asp Leu Met Glu Thr Asp Leu Tyr Lys Leu Leu Lys Ser Gln
            100                 105                 110
Gln Leu Ser Asn Asp His Ile Cys Tyr Phe Leu Tyr Gln Ile Leu Arg
            115                 120                 125
Gly Leu Lys Tyr Ile His Ser Ala Asn Val Leu His Arg Asp Leu Lys
        130                 135                 140
Pro Ser Asn Leu Leu Ile Asn Thr Thr Cys Asp Leu Lys Ile Cys Asp
145                 150                 155                 160
Phe Gly Leu Ala Arg Ile Ala Asp Pro Glu His Asp His Thr Gly Phe
                165                 170                 175
Leu Thr Glu Tyr Val Ala Thr Arg Trp Tyr Arg Ala Pro Glu Ile Met
            180                 185                 190
Leu Asn Ser Lys Gly Tyr Thr Lys Ser Ile Asp Ile Trp Ser Val Gly
            195                 200                 205
Cys Ile Leu Ala Glu Met Leu Ser Asn Arg Pro Ile Phe Pro Gly Lys
210                 215                 220
His Tyr Leu Asp Gln Leu Asn His Ile Leu Gly Ile Leu Gly Ser Pro
225                 230                 235                 240
Ser Gln Glu Asp Leu Asn Cys Ile Ile Asn Met Lys Ala Arg Asn Tyr
                245                 250                 255
Leu Gln Ser Leu Pro Ser Lys Thr Lys Val Ala Trp Ala Lys Leu Phe
            260                 265                 270
Pro Lys Ser Asp Ser Lys Ala Leu Asp Leu Leu Asp Arg Met Leu Thr
            275                 280                 285
Phe Asn Pro Asn Lys Arg Ile Thr Val Glu Glu Ala Leu Ala His Pro
        290                 295                 300
Tyr Leu Glu Gln Tyr Tyr Asp Pro Thr Asp Glu Pro Val Ala Glu Glu
```

-continued

```
                305                 310                 315                 320
Pro Phe Thr Phe Ala Met Glu Leu Asp Asp Leu Pro Lys Glu Arg Leu
                    325                 330                 335

Lys Glu Leu Ile Phe Gln Glu Thr Ala Arg Phe Gln Pro Gly Val Leu
                    340                 345                 350

Glu Ala Pro
        355

(2) INFORMATION FOR SEQ ID NO: 9 :

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 9:

Gly Ala Ala Ala Glu Arg Arg Ala Gln Arg Gly Gly Gly Gly Gly Gly
1               5                   10                  15

Pro Ala Asn Met Ala Ala Ala Ala Ala Gly Ala Gly Pro Glu
            20                  25                  30

Met Val Arg Gly Gln Val Phe Asp Val Gly Pro Arg Tyr Thr Asn Leu
            35                  40                  45

Ser Tyr Ile Gly Glu Gly Ala Tyr Gly Met Val Cys Ser Ala Tyr Asp
    50                  55                  60

Asn Val Asn Lys Val Arg Val Ala Ile Lys Lys Ile Ser Pro Phe Glu
65                  70                  75                  80

His Gln Thr Tyr Cys Gln Arg Thr Leu Arg Glu Ile Lys Ile Leu Leu
                85                  90                  95

Arg Phe Arg His Glu Asn Ile Ile Gly Ile Asn Asp Ile Ile Gln Ala
            100                 105                 110

Pro Thr Ile Glu Gln Met Lys Asp Val Tyr Ile Val Gln Asp Leu Met
            115                 120                 125

Glu Thr Asp Leu Tyr Lys Leu Leu Lys Thr Gln His Leu Ser Asn Asp
    130                 135                 140

His Ile Cys Tyr Phe Leu Tyr Gln Ile Leu Arg Gly Leu Lys Tyr Ile
145                 150                 155                 160

His Ser Ala Asn Val Leu His Arg Asp Leu Lys Pro Ser Asn Leu Leu
                165                 170                 175

Leu Asn Thr Thr Cys Asp Leu Lys Ile Cys Asp Phe Gly Leu Ala Arg
            180                 185                 190

Val Ala Asp Pro Asp His Asp His Thr Gly Phe Leu Thr Glu Tyr Val
            195                 200                 205

Ala Thr Arg Trp Tyr Arg Ala Pro Glu Ile Met Leu Asn Ser Lys Gly
    210                 215                 220

Tyr Thr Lys Ser Ile Asp Ile Trp Ser Val Gly Cys Ile Leu Ala Glu
225                 230                 235                 240

Met Leu Ser Asn Arg Pro Ile Phe Pro Gly Lys His Tyr Leu Asp Gln
                245                 250                 255

Leu Asn His Ile Leu Gly Ile Leu Gly Ser Pro Ser Gln Glu Asp Leu
            260                 265                 270

Asn Cys Ile Ile Asn Leu Lys Ala Arg Asn Tyr Leu Leu Ser Leu Pro
            275                 280                 285

His Lys Asn Lys Val Pro Trp Asn Arg Leu Phe Pro Asn Ala Asp Ser
    290                 295                 300
```

```
Lys Ala Leu Asp Leu Leu Asp Lys Met Leu Thr Phe Asn Pro His Lys
305                 310                 315                 320

Arg Ile Glu Val Glu Gln Ala Leu Ala His Pro Tyr Leu Glu Gln Tyr
                325                 330                 335

Tyr Asp Pro Ser Asp Glu Pro Ile Ala Glu Ala Pro Phe Lys Phe Asp
                340                 345                 350

Met Glu Leu Asp Asp Leu Pro Lys Glu Lys Leu Lys Glu Leu Ile Phe
                355                 360                 365

Glu Glu Thr Ala Arg Phe Gln Pro Gly Tyr Arg Ser
                370                 375                 380
```

(2) INFORMATION FOR SEQ ID NO: 10 :

(i) SEQUENCE CHARACTERISTICS:
        (A) LENGTH: 586 amino acids
        (B) TYPE: amino acid
        (D) TOPOLOGY: linear (ii) MOLECULE TYPE: protein (xi) SEQUENCE DESCRIPTION: SEQ ID NO: 10:

```
Gly Ala Arg Gly Arg Pro Leu Ala Glu Thr Trp Pro Phe Leu Thr Ala
1               5                   10                  15

Pro Val Leu Pro Gly Gln Leu Gln Ile Thr Glu Pro Thr Met Ala Glu
                20                  25                  30

Lys Gly Asp Cys Ile Ala Ser Val Tyr Gly Tyr Asp Leu Gly Gly Arg
                35                  40                  45

Phe Val Asp Phe Gln Pro Leu Gly Phe Gly Val Asn Gly Leu Val Leu
50                  55                  60

Ser Ala Val Asp Ser Arg Ala Cys Arg Lys Val Ala Val Lys Lys Ile
65                  70                  75                  80

Ala Leu Ser Asp Ala Arg Ser Met Lys His Ala Leu Arg Glu Ile Lys
                85                  90                  95

Ile Ile Arg Arg Leu Asp His Asp Asn Ile Val Lys Val Tyr Glu Val
                100                 105                 110

Leu Gly Pro Lys Gly Thr Asp Leu Gln Gly Glu Leu Phe Lys Phe Ser
                115                 120                 125

Val Ala Tyr Ile Val Gln Glu Tyr Met Glu Thr Asp Leu Ala Arg Leu
                130                 135                 140

Leu Glu Gln Gly Thr Leu Ala Glu Glu His Ala Lys Leu Phe Met Tyr
145                 150                 155                 160

Gln Leu Leu Arg Gly Leu Lys Tyr Ile His Ser Ala Asn Val Leu His
                165                 170                 175

Arg Asp Leu Lys Pro Ala Asn Ile Phe Ile Ser Thr Glu Asp Leu Val
                180                 185                 190

Leu Lys Ile Gly Asp Phe Gly Leu Ala Arg Ile Val Asp Gln His Tyr
                195                 200                 205

Ser His Lys Gly Tyr Leu Ser Glu Gly Leu Val Thr Lys Trp Tyr Arg
                210                 215                 220

Ser Pro Arg Leu Leu Leu Ser Pro Asn Asn Tyr Thr Lys Ala Ile Asp
225                 230                 235                 240

Met Trp Ala Ala Gly Cys Ile Leu Ala Glu Met Leu Thr Gly Arg Met
                245                 250                 255

Leu Phe Ala Gly Ala His Glu Leu Glu Gln Met Gln Leu Ile Leu Glu
                260                 265                 270
```

```
Thr Ile Pro Val Ile Arg Glu Glu Asp Lys Asp Glu Leu Leu Arg Val
        275                 280                 285

Met Pro Ser Phe Val Ser Ser Thr Trp Glu Val Lys Arg Pro Leu Arg
    290                 295                 300

Lys Leu Leu Pro Glu Val Asn Ser Glu Ala Ile Asp Phe Leu Glu Lys
305                 310                 315                 320

Ile Leu Thr Phe Asn Pro Met Asp Arg Leu Thr Ala Glu Met Gly Leu
                325                 330                 335

Gln His Pro Tyr Met Ser Pro Tyr Ser Cys Pro Glu Asp Glu Pro Thr
            340                 345                 350

Ser Gln His Pro Phe Arg Ile Glu Asp Glu Ile Asp Ile Val Leu
        355                 360                 365

Met Ala Ala Asn Gln Ser Gln Leu Ser Asn Trp Asp Thr Cys Ser Ser
    370                 375                 380

Arg Tyr Pro Val Ser Leu Ser Ser Asp Leu Glu Trp Arg Pro Asp Arg
385                 390                 395                 400

Cys Gln Asp Ala Ser Glu Val Gln Arg Asp Pro Arg Gly Phe Gly Ala
                405                 410                 415

Leu Ala Glu Asp Val Gln Val Asp Pro Arg Lys Asp Ser His Ser Ser
            420                 425                 430

Ser Glu Arg Phe Leu Glu Gln Ser His Ser Ser Met Glu Arg Ala Phe
        435                 440                 445

Glu Ala Asp Tyr Gly Arg Ser Cys Asp Tyr Lys Val Gly Ser Pro Ser
    450                 455                 460

Tyr Leu Asp Lys Leu Leu Trp Arg Asp Asn Lys Pro His His Tyr Ser
465                 470                 475                 480

Glu Pro Lys Leu Ile Leu Asp Leu Ser His Trp Lys Gln Ala Ala Gly
                485                 490                 495

Ala Pro Pro Thr Ala Thr Gly Leu Ala Asp Thr Gly Ala Arg Glu Asp
            500                 505                 510

Glu Pro Ala Ser Leu Phe Leu Glu Ile Ala Gln Trp Val Lys Ser Thr
        515                 520                 525

Gln Gly Ala Gln Ser Thr Pro Ala Arg Pro Pro Thr Thr Pro Ser Ala
    530                 535                 540

Ala Cys Leu Pro Arg Pro Pro Pro Gly Pro Gly Arg Arg
545                 550                 555                 560

Gln Pro Pro Val Arg Pro Gly Arg Val His Leu Pro Arg Pro Glu Ala
                565                 570                 575

Leu His Gln Ala Arg Gly Pro Ala Gly Gln
            580                 585

(2) INFORMATION FOR SEQ ID NO: 11 :

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 11:

Val Ala Ile Lys Lys
1               5
```